United States Patent
Guevara et al.

[11] Patent Number: 6,086,571
[45] Date of Patent: Jul. 11, 2000

[54] ABSORBENT ARTICLE WITH RESPIRABLE ELASTIC BELT WITH HIGH STRETCH AND RETRACTION CAPACITY

[75] Inventors: Cesar Montemayor Guevara; Carlos Eduardo Richer Cantu; Martin Juarez Zamacona, all of Nuevo Leon, Mexico

[73] Assignee: Absormex S.A. de C.V., Nuevo Leon, Mexico

[21] Appl. No.: 08/935,824

[22] Filed: Sep. 23, 1997

[30] Foreign Application Priority Data

May 26, 1997 [MX] Mexico .................................. 973855

[51] Int. Cl.⁷ .................................................. A61F 13/20
[52] U.S. Cl. ........................................ 604/385.2; 604/386
[58] Field of Search ................................ 604/385.1–386, 604/389, 390, 391, 392, 393, 394, 396

[56] References Cited

U.S. PATENT DOCUMENTS

| | | |
|---|---|---|
| H1674 | 8/1997 | Ames ........................................ 604/386 |
| Re. 26,151 | 1/1967 | Duncan et al. . |
| 3,860,003 | 1/1975 | Buell . |
| 3,911,173 | 10/1975 | Sprague, Jr. . |
| 4,051,853 | 10/1977 | Egan, Jr. . |
| 4,066,081 | 1/1978 | Schaar . |
| 4,315,568 | 2/1982 | Bolick ...................................... 604/392 |
| 4,573,986 | 3/1986 | Minetola et al. . |
| 4,646,362 | 3/1987 | Heron et al. ........................... 604/385.2 |
| 4,785,996 | 11/1988 | Ziecker et al. . |
| 4,787,897 | 11/1988 | Torimae et al. . |
| 4,795,456 | 1/1989 | Borgers et al. . |

(List continued on next page.)

FOREIGN PATENT DOCUMENTS

| | | |
|---|---|---|
| 0487758 | 6/1992 | European Pat. Off. ................ 604/386 |
| 532 034 | 3/1993 | European Pat. Off. . |
| 532 035 | 3/1993 | European Pat. Off. . |
| 2606257 | 5/1988 | France .................................... 604/386 |

OTHER PUBLICATIONS

"New Functional Materials for Absorbent Products" by Suzuki, New Nonwovens World, Fall 1993, pp. 77–85.
Report in "Consumer Report" by Sensor Company, Oct. 1995.
"New Facility, New Concept for Hot Melt Machinery Supplier", by Carl Cucuzza, Nonwovens Industry, Jan. 1995.
"Quality does Not Have to Be Expensive" by Bouda, Nonwovens Industry, Jan. 1995.
"1994 Private Label Trade Show Review", Staff Report, Nonwovens World, Spring 1995, pp. 85–87.
"K–C Introduces Stretch Sides", article in Nonwovens World, Spring 1995, pp. 39–40.

*Primary Examiner*—Mark O. Polutta
*Attorney, Agent, or Firm*—Sughrue, Mion, Zinn, Macpeak & Seas, PLLC

[57] ABSTRACT

An absorbent article including a containment assembly having a topsheet, a backsheet and an absorbent core placed between the topsheet and the backsheet. First and second extension ears extend laterally outwards from each one of the corresponding lengthwise edges of the containment assembly in the rear waist region, each one of the first and second extension ears have a close edge connected to the rear waist region, and a distant edge laterally separated outwards from the close edge. First and second elastic belts extend laterally outwards from each one of the corresponding lengthwise edges of the containment assembly in the rear waist region, or from each one of the corresponding extension ears. One of the first and second elastic belts has a close edge connected to the rear waist region, or to the distant edges of the first and second extension ears, and a distant edge laterally separated outwards from the close edge, the tying media being connected at the distant edge. The elastic belts have a structure which includes a top nonwoven layer portion, a back nonwoven layer portion and a layer portion of elastomer threads placed between the top and back nonwoven layer portions, jointly forming the elastic belts, which provide a maximum elasticity up to 500%, and in which the material of the top and back nonwoven layer portions provide an increased respirability characteristic.

10 Claims, 18 Drawing Sheets

U.S. PATENT DOCUMENTS

| | | |
|---|---|---|
| 4,826,499 | 5/1989 | Ahr . |
| 4,842,666 | 6/1989 | Werenicz . |
| 4,964,860 | 10/1990 | Gipson et al. . |
| 5,151,092 | 9/1992 | Buell et al. . |
| 5,246,433 | 9/1993 | Hasse et al. . |
| 5,304,162 | 4/1994 | Kuen ........ 604/392 |
| 5,358,500 | 10/1994 | Lavon et al. ........ 604/386 |
| 5,383,871 | 1/1995 | Carlin et al. . |
| 5,411,498 | 5/1995 | Fahrenkrug et al. ........ 604/392 |
| 5,518,801 | 5/1996 | Chappell et al. . |
| 5,706,524 | 1/1998 | Herrin et al. ........ 604/393 |

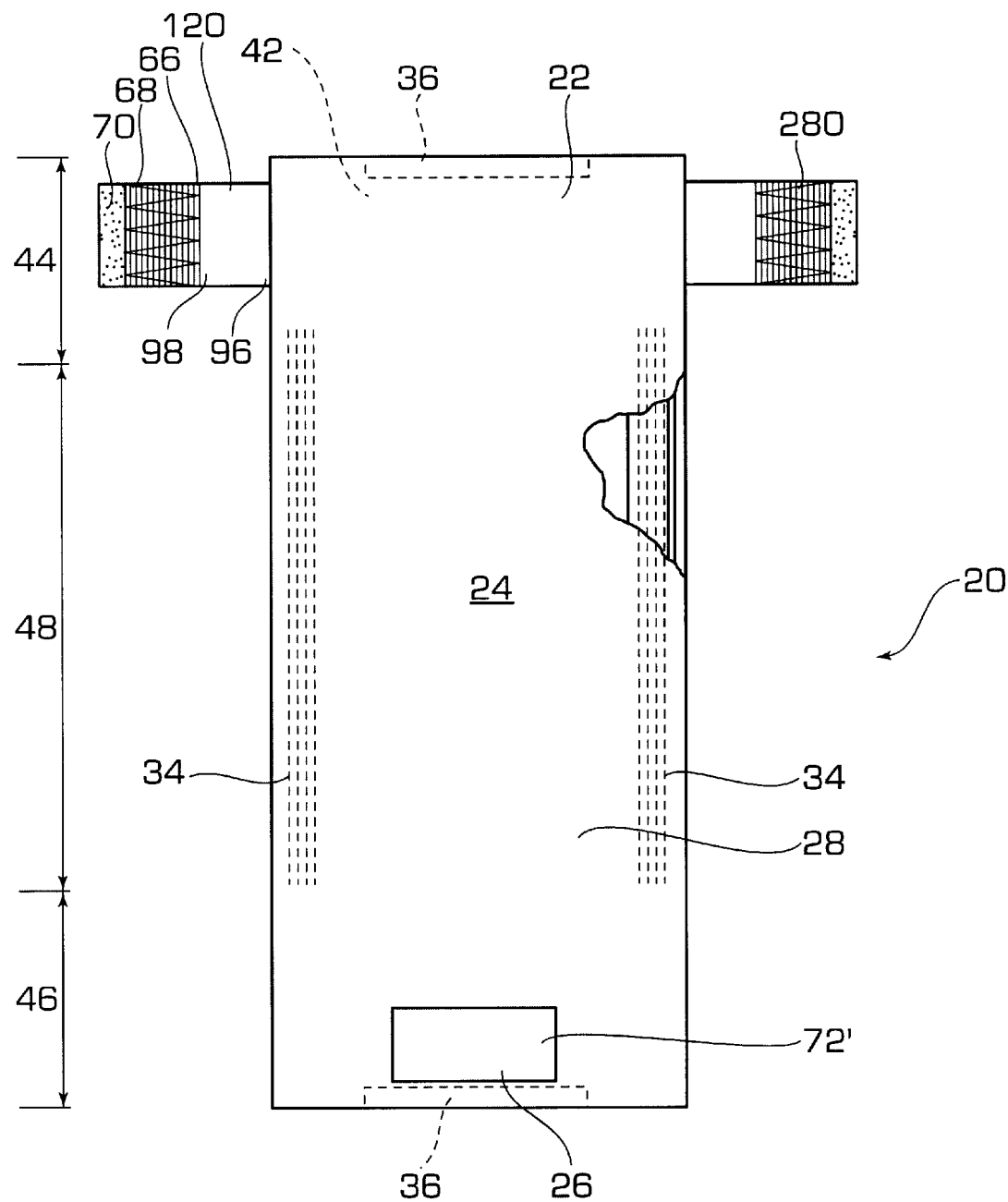

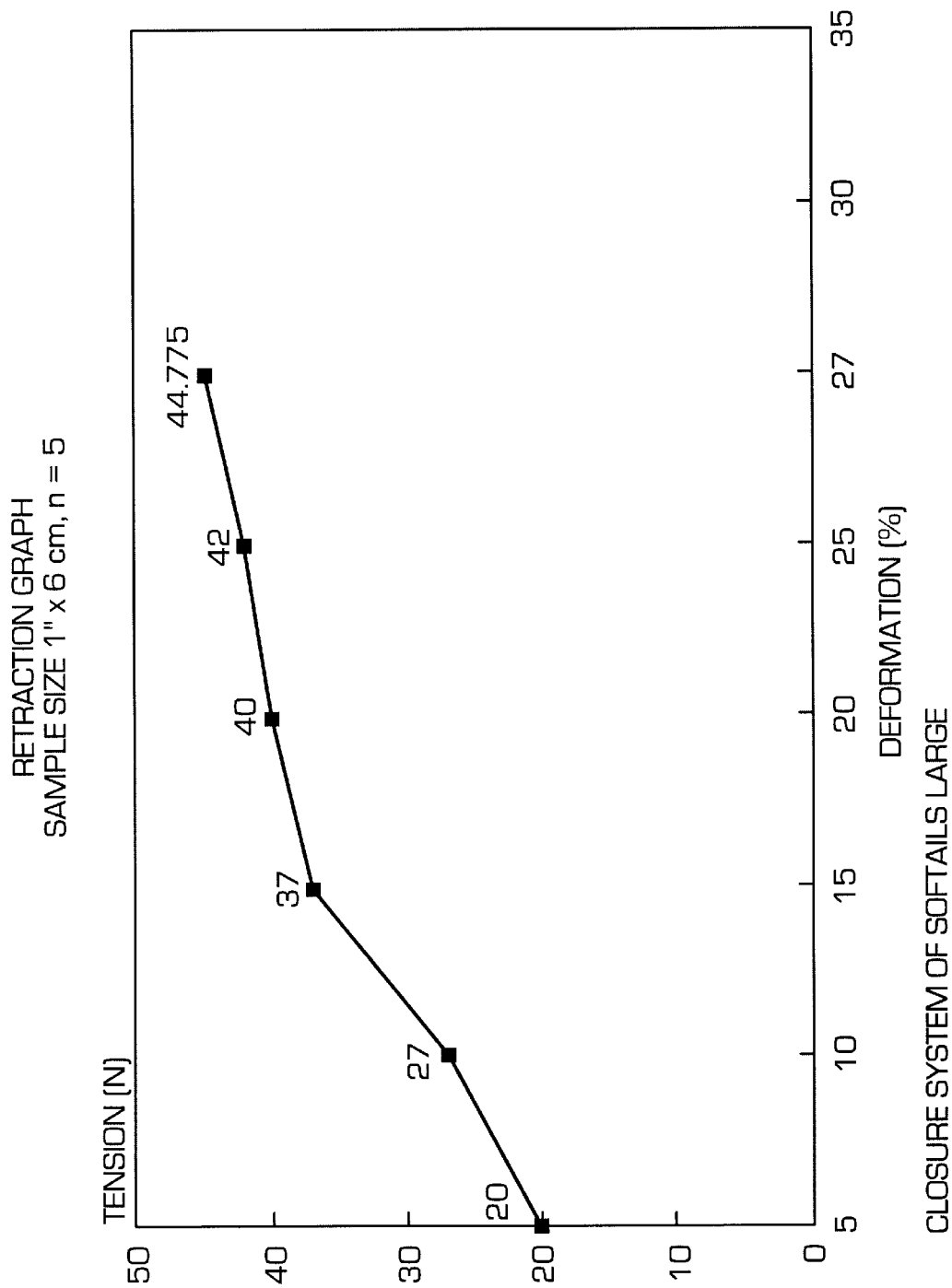

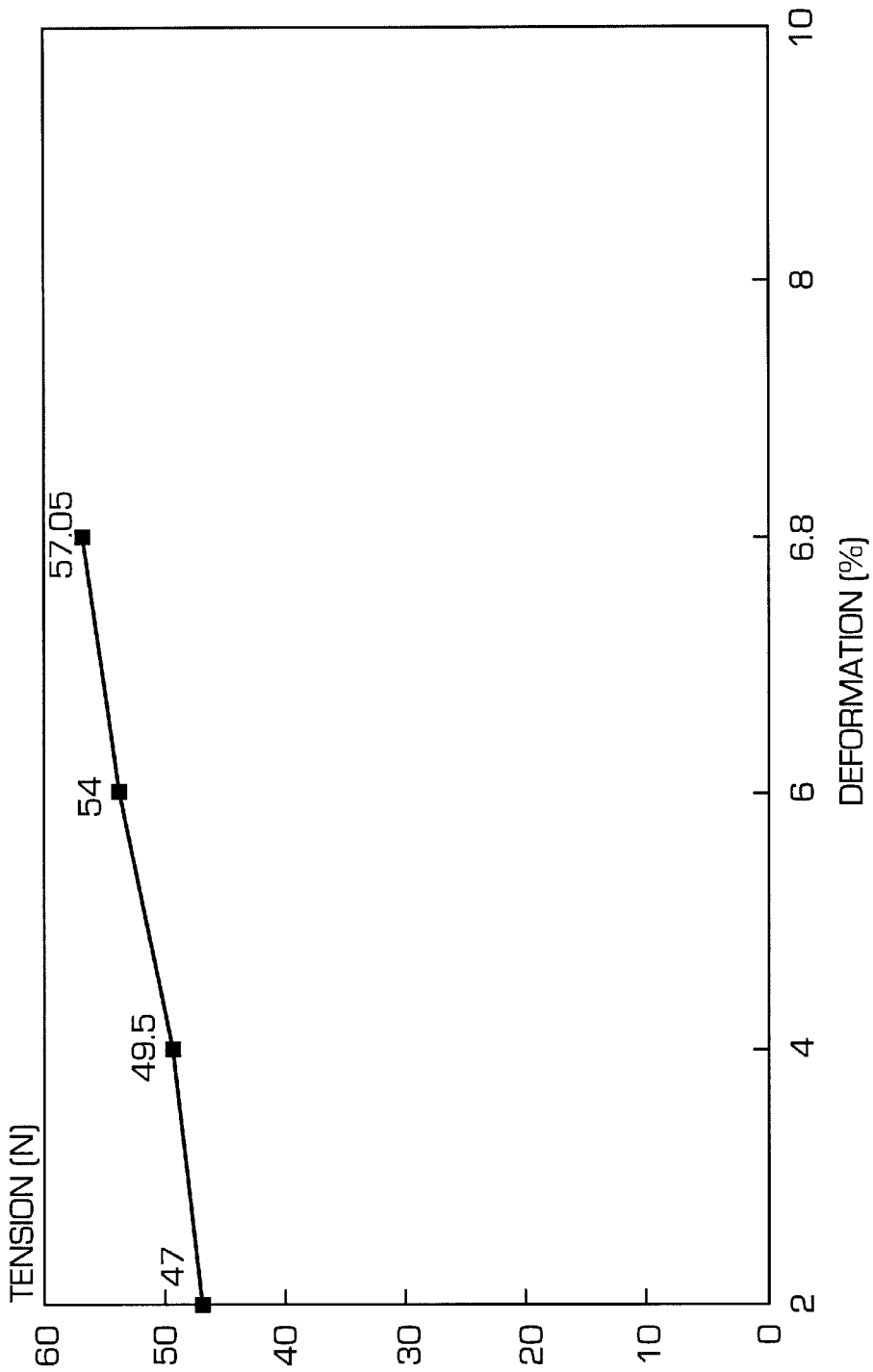

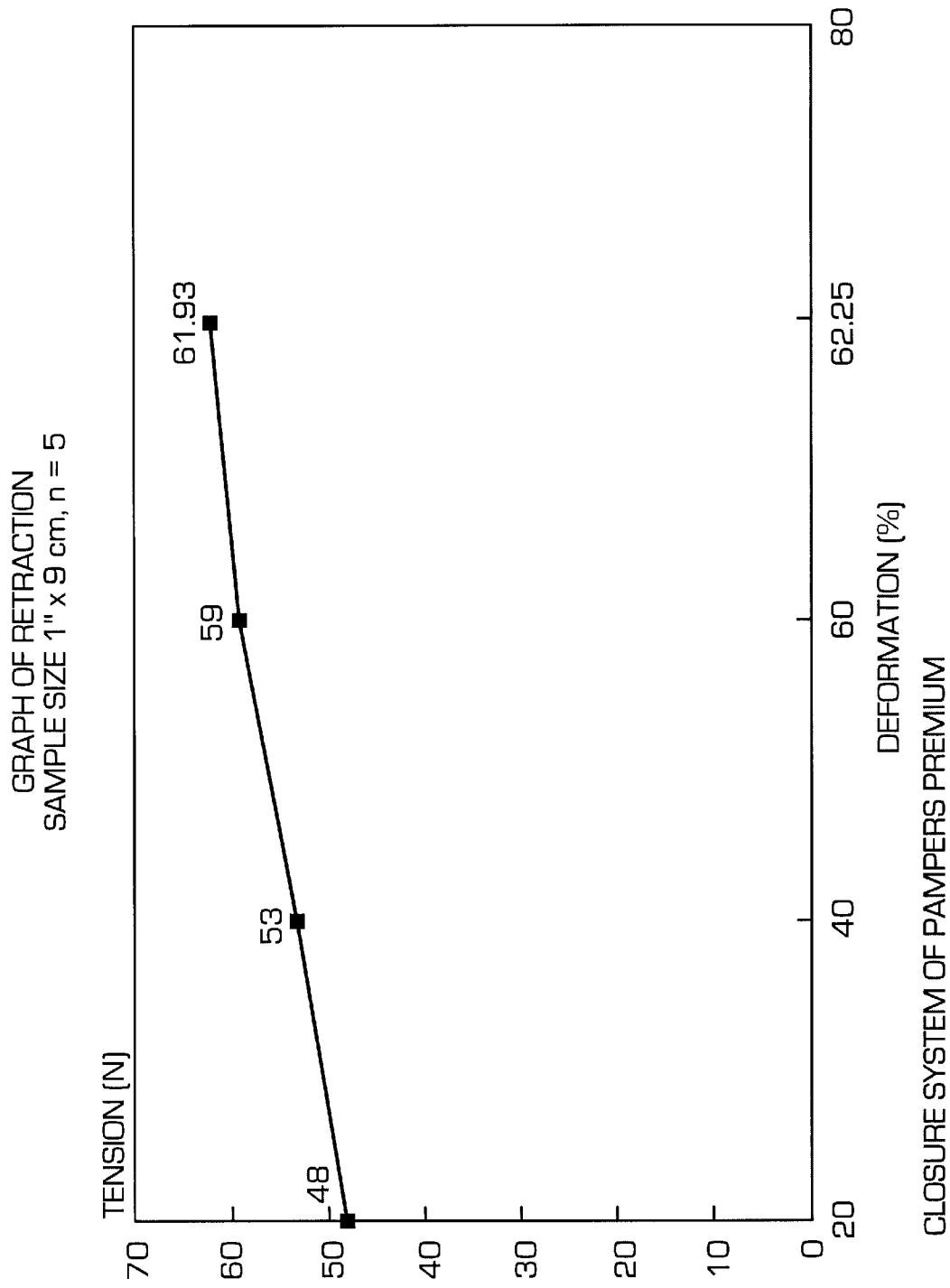

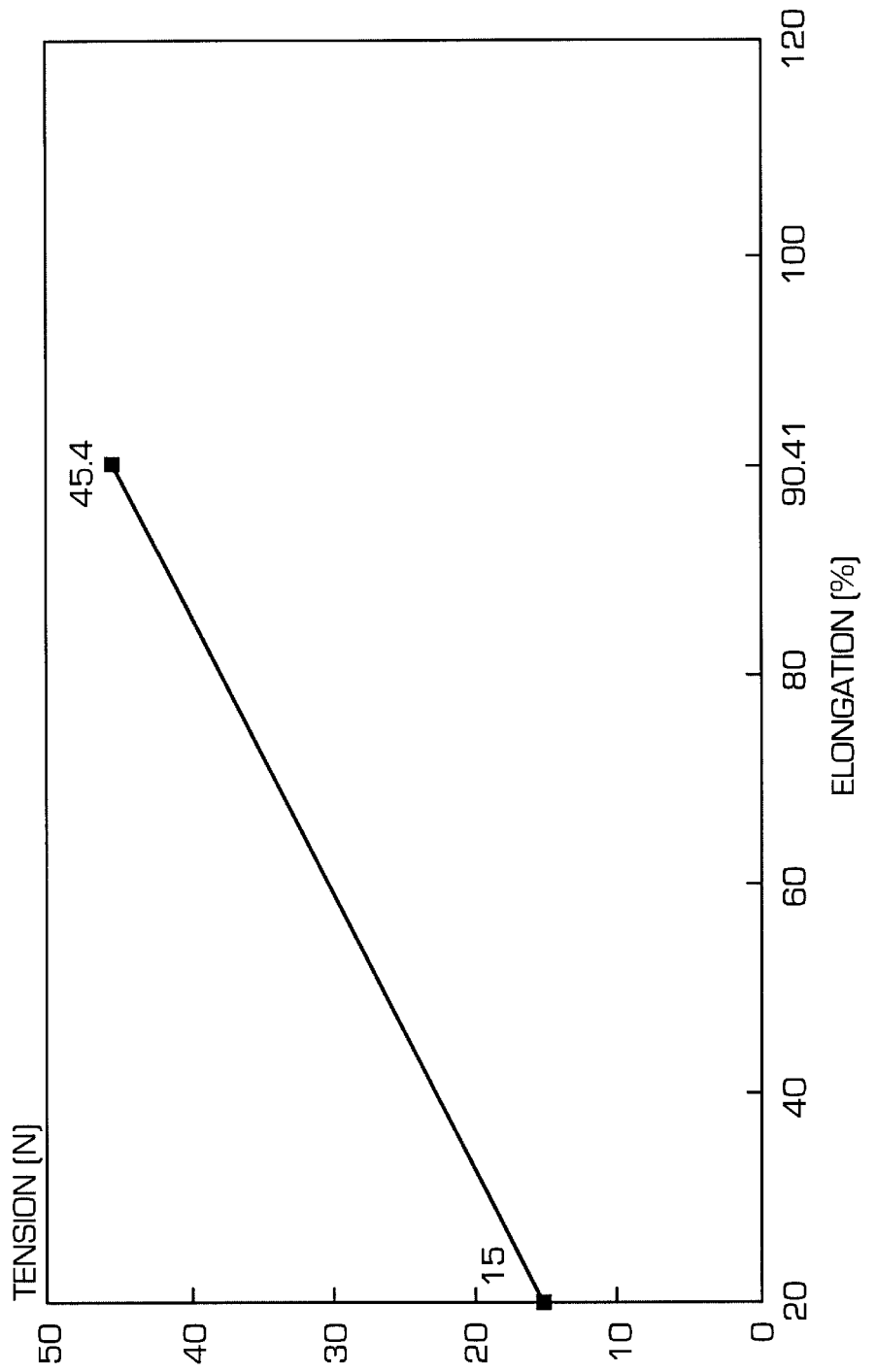

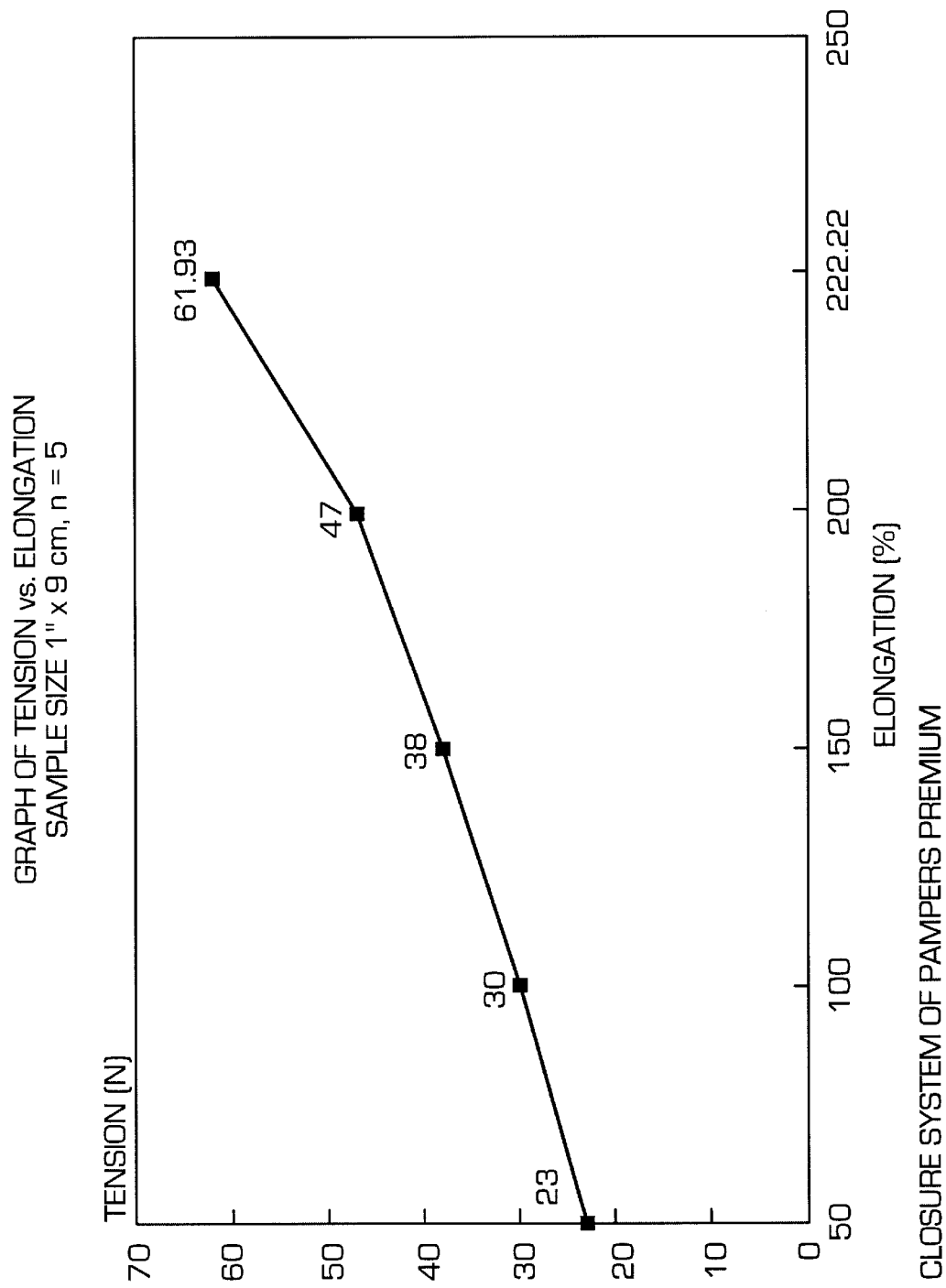

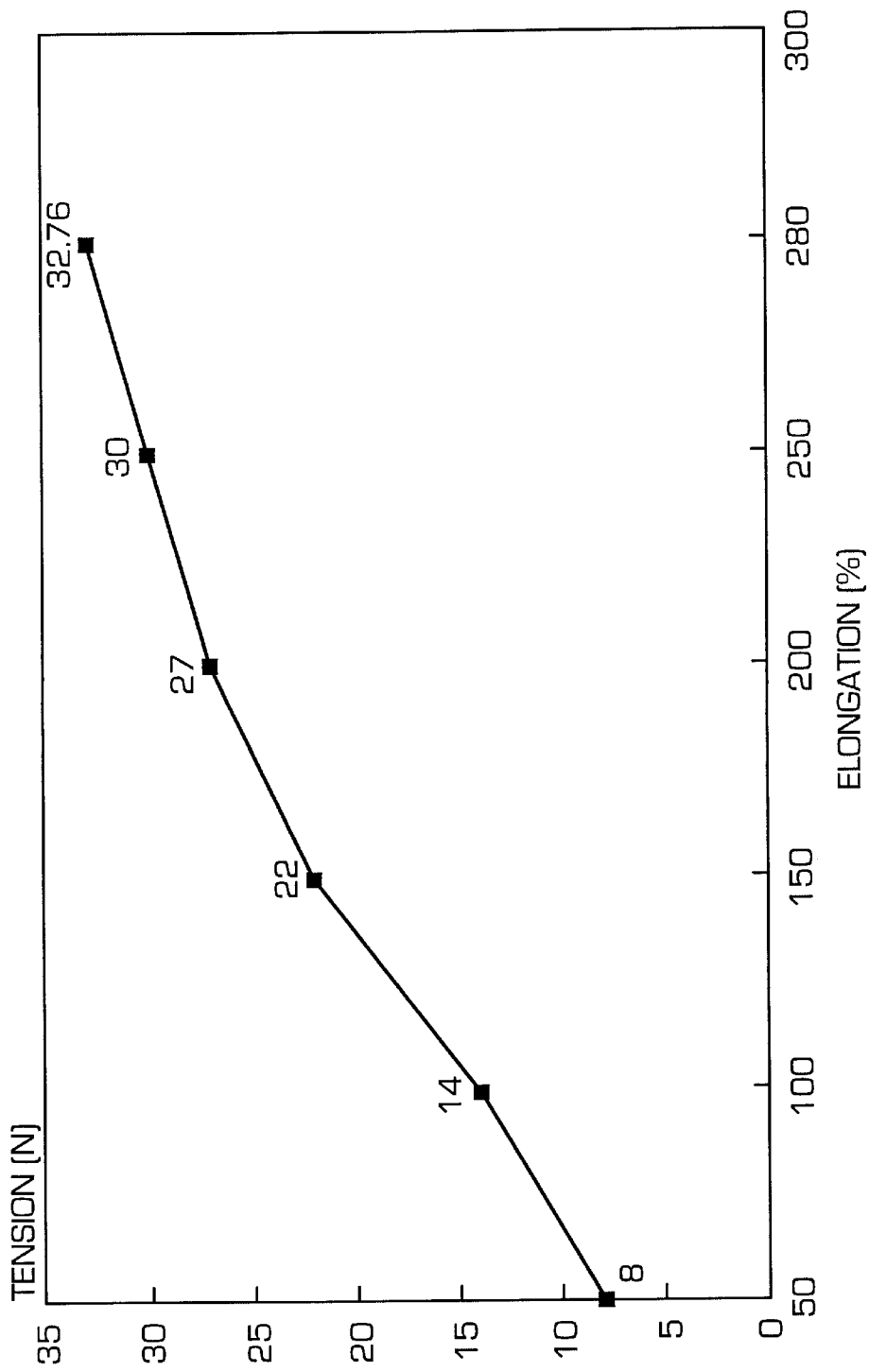

ABSORBENT ARTICLE WITH RESPIRABLE ELASTIC BELT WITH HIGH STRETCH AND RETRACTION CAPACITY

FIELD OF THE INVENTION

This invention refers to absorbent articles such as diapers, support briefs for the incontinent, diaper supports, training pants and similar, and more particularly, absorbent articles with gripping elements to adapt to the user's waist.

BACKGROUND OF THE INVENTION

From the incipience of disposable absorbent articles for sanitary applications on infants, and subsequently to alleviate problems of incontinency in adults, manufacturers of these products have focused over a long period of time on a continual improvement in the fabrication of the absorbent core, conforming to traditional methods in the design of gripping elements to adjust the product to the user's body and the comfort provided to them.

Babies and other incontinent individuals use absorbent articles, such as diapers, to receive and contain urine and other body eliminations. Absorbent articles operate both to contain materials eliminated from the body and absorb discharges from the user's body and avoid leaking and spotting of the user's garments and bed clothes. In the technique disposable absorbent articles with different designs are known. For example, U.S. Pat. No. Re. 26,151 entitled "Disposable Diaper", issued to Duncan and Backer on Jan. 31, 1967, describes a conventional disposable diaper which has enjoyed great acceptance throughout the world and has been commercially successful. In addition, U.S. Pat. No. 4,964,860 entitled DETACHABLE TWO-PIECE ABSORBENT GARMENT, issued to Gipson and others on Oct. 23, 1990 describes an absorbent article with a band. U.S. Pat. No. 5,246,433 entitled ELASTICIZED DISPOSABLE TRAINING PANT AND METHOD OF MAKING THE SAME, issued to Hasse and others on Sep. 21, 1993 describes a unitary disposable absorbent article which can be used as training pants. Nevertheless, absorbent articles currently available to the public fail to provide many of the benefits which can be obtained with absorbent articles that have elastic gripping elements to allow the user to select the design of a diaper most appropriate for each particular use.

In the current market, the consumer has innumerable different basic designs of absorbent articles such as diapers to choose from, depending on the different options, comfort and cost, including conventional diapers, diapers with a band and training pants of the "pull-up" type. Conventional designs of diapers are generally of a type less expensive to produce and are generally accepted for use by babies and the sick or persons who in one way or another are bed-ridden. A conventional diaper adjusts to the user, first placing the rear portion of the diaper under the user (generally, the rear portion of the diaper is placed under the gluteal region of the body and the rear waist of the user) and then the rest of the diaper is pulled through the user's legs. The rear portion of the diaper is then connected to the front waist portion of the diaper over each side of the user by gripping means. Nevertheless, said conventional configurations tend to be very difficult to use, when the user refuses to remain still during the time the diaper is being applied. Moreover, adult users normally find that absorbent articles of the conventional type are difficult to put on by themselves without help. In addition, the configuration of the absorbent article lacks an easy inspection method without the complete removal of the absorbent article.

Diapers with a band have been introduced to overcome certain of the problems existing with conventional-type diapers. Diapers with a band are generally adjusted to the user by placing the diaper in such manner as to allow the band to be adjusted around the user's waist and the rest of the diaper hanging down between the user's legs. The portion of the diaper that hangs from the waist is then pulled through the legs of the user and connected to the the band portion of the diaper close to the waist. This way, the diaper with band can be adjusted to users who are standing and can be easily inspected to see if it is dirty without completely removing the diaper. In addition, adult users regularly find that the designs of absorbent articles with a band are much easier to put on without assistance. Nevertheless, as a general rule diapers with a band are more costly than conventional diapers and some users prefer the conventional design to the design with a band.

The trend of manufacturers to provide products that significantly improve the comfort provided to users is reflected, for example, in the generation of products which on the outside give the appearance of clothing (East Coast of the United States, at the beginning of 1995, according to the magazine Nonwovens Industry, page 39, January 1995 edition), and lateral elastic ties which provide the user with an anatomical adjustment.

European patent No. 0 532 035 issued to Zehnerm Rosch, Odorzynski, Siebers and Blenke on Mar. 17, 1993, entitled "absorbent article for recently born babies, adjustable in length by a foldable absorbent panel at the front side of the diaper and adjustable at the baby's waist by means of ear members that can be overlapped, one over the other and tied at the front of the diaper", is an example of said trend.

European patent No. 0 532 034 issued to Mary Bruemmer on Mar. 17, 1993, describes a disposable absorbent garment which includes a pair of ear members stretchable differentially, composed of an inner stretchable section and an outer stretchable section.

The above mentioned European patents refer to gripping elements that allow the article to adapt, by tension, to the user's waist. However, they do not mention the disadvantages of the effect of the continual movement of the user in respect to the adjustments at the waist; that is, the slipping away of the absorbent core from the areas to be protected.

U.S. Pat. No. 5,383,871 issued to Edward Carlin on Jan. 24, 1995 claims absorbent articles containing a fastening system that provides a sustained dynamic adjustment.

A wide range of fastening systems for absorbent products is known in the state of the art, particularly elastic gripping means to hold the absorbent article to the user's waist, and provide an anatomical adjustment, as claimed in U.S. Pat. No. 4,051,853 entitled "DIAPER WITH EXTENSIBLE FASTENER", issued to Francis L. Egan Jr. on Oct. 4, 1977; U.S. Pat. No. 4,066,081 entitled DIAPER WITH EXTENSIBLE FASTENER, issued to Charles H. Schaer on Jan. 3, 1978; U.S. Pat. No. 4,787,897 entitled STRETCHABLE FASTENING TAPE FOR DISPOSABLE DIAPER issued to Yasuhiro Torimae and others on Nov. 29, 1988; U.S. Pat. No. 4,795,456 entitled STRETCHABLE DIAPER TAB issued to Leo Borgers and others on Jan. 3, 1989; and U.S. Pat. No. 4,826,499 entitled ABSORBENT GARMENT HAVING LATERALLY DISPLACEABLE FASTENING MEANS issued to Nicholas A. Ahr on May 2, 1989. However, said gripping means described in the above mentioned patent have disadvantage in terms of their reduced capacity to stretch lengthwise and their retraction capacity.

Moreover, said anatomical adjustment concepts using stretch elements have been being applied together with traditional concepts of various sizes of absorbent products, containing very wide construction elements, which induces the consumer to confusion because of the presence of so many products on the shelves (up to 6 different stages of the same diaper), and increases the manufacturing cost, because of needing so much stock of raw material to prepare each one of these stages of absorbent products.

Recently, the Procter & Gamble company launched its diaper on the market under the brand "Pampers Uni Futur", which provides characteristics of a flexible fastening system (flexiband), reduction of materials on the outer and inner coverings (v.gr., the topsheet and the backsheet), core with a straight and shorter design than the traditional diaper, promoting in their marketing "perfect expansion and adaptation" to the body of babies. This product is offered at very competitive prices in respect to the other diapers for babies in the economic niche of the market. Nevertheless, the flexible concept offered by this product is very limited; since the flexiband element is formed by the napped joining of the polyethylene and polypropylene film, known as SELF woven (structural elastic like-film), the maximum stretching obtained at the time of fastening the diaper is approximately between 33% and 35% per flexible element. The results obtained in dynamic laboratories or consumers panels in samples of the general consumer in this niche showed negative acceptance results in the first instance, due to irritation problems of the skin caused by the friction of the flexiband, escape of liquids and solids because of the reduced length of the absorbent core, and the lack of adaptation to the bikini concept suggested by the product. This information was obtained from the report presented by the Sensor company in October 1995, which is incorporated by reference herein.

Other products that embodied elastic fastening elements were the diapers sold under the brands "Huggies Extratrim" and "Supreme" manufactured by Kimberly-Clark Corporation as claimed in U.S. Pat. No. 3,800,769 issued to E. Jacuba on Apr. 2, 1974, and U.S. Pat. No. 5,518,801 issued to Chappell on May 21, 1996. These products incorporate elastomer materials in the form of elastic bands which allow for a more comfortable adjustment to the baby's waist. Nevertheless, these elements are obtained from a coextrusion of materials, or through the connection of fusion and blown applied elastomers and provide a maximum stretching of only up to 75% in each gripping element (ultra-elastic). Nevertheless, these elastic fastening elements present a disadvantage on not offering respirability, since most of them are produced on the basis of laminations.

In the Nonwovens World magazine, Autumn 1993, Dr. Migaku Susuki in the publication of the Article "New Functional Material for Absorbent Products" stated that "improvements in cost performance include the combination of comfort with special materials and reduced weight and reduced quantity of raw materials in the finished product, in addition to the fact that consideration must be given to requirements for environment friendly products (social impact) and the need for innovation in the market". In another article published in the Nonwovens Industry magazine, January 1995, entitled "New Facility, New Concept for Hot-Melt Machinery Supplier", Dr. Carl Cucuzza states that "retailers pressured manufacturers searching for a quicker reply to purchase orders, products focused on the clients and improvements in the consistency and quality of the product. As a result, the manufacturers should balance efficiency against capital expenses, reduced inventories of the finished product and raw material, a reduction of wastes and idle time of equipment".

Notwithstanding the efforts made to manufacture an absorbent product with improved elasticity properties at the waist and respirability characteristics of the elastic gripping elements to adapt to the user's waist, the inclusion of elements that can provide elasticity percentages above 75% is advisable and necessary, limited by the elastomer materials described in the state of the art, in order to reduce the number of materials used in the manufacture of a diaper, without sacrificing adjustment and comfort.

Moreover, in line with the concept expressed by Dr. Susuki of "environment friendly", said materials should have "respirability" characteristics. In the Nonwovens World magazine, published in October 1993, Tim Woodbridge defined in an article that respirability "occurs when the delaying medium (air or water steam) can pass through the material membrane at such rate as to maintain an adequate balance for the designed final use". In the Spring of 1995, the company called Confab/ICD published an article in the Nonwovens World magazine, which announced a material which "is very similar to an elastic waist band" for its diaper for incontinent adults."

It would be advantageous to provide a disposable absorbent article such as a diaper with elastic gripping elements to allow the user to place and hold the absorbent article adjusted to and comfortable for the person's waist.

Consequently, the object of this invention is to provide an absorbent article with elastic gripping elements with superior elasticity characteristics, mainly in the fastening system, of up to 250% and increased respirability.

Another object of this invention is to provide an absorbent article which adjusts to the majority of users' sizes, ideally, 2 sizes thereof, not more than three.

Still another object of this invention is to provide an absorbent article substantially more economic than current conventional absorbent articles, but which embodies certain elements of the expensive absorbent articles.

Another object of this invention is to provide an absorbent article with a self adjustable gripping system designed to allow the absorbent article to be placed in a conventional configuration, or structured in such way as to form a type of pull-up training pants.

Still another object of this invention is to provide a disposable absorbent article that does not require material changes in the production lines.

These and other objects of this invention will be more easily observed by referring to the following description taken together with the attached drawings.

BRIEF DESCRIPTION OF THE INVENTION

This invention refers to disposable absorbent articles, such as disposable diapers, underpants for the incontinent, training pants and similar, which have elastic gripping elements that provide the user with various options for putting them on and adjusting them. The elastic gripping elements allow the user to select between diapers with conventional configurations, with a band and which "pull up". In addition, the elastic gripping elements are designed to change and easily remove the absorbent article as well as an easy inspection to see if it is dirty. Said absorbent articles including a containment assembly which has an outer surface which faces away from the user, an inner surface which faces toward the user, a rear waist region, a front waist region and a region between the legs between said front and rear waist regions, a pair of lengthwise edges; said contention assembly includes a topsheet permeable to liquid; a backsheet impermeable to liquid; and an absorbent core placed between the topsheet and the backsheet; elastic leg devices located in the area between the legs of the absorbent article; as an option, first and second extension ears each one of them having a close edge joined to said rear region of the waist, and a distant edge separated outwards from said closed edge; first and second elastic belts which wrap around part of the user's waist; gripping devices; and at least one landing band; in which each of the first and second elastic belts extends laterally outwards from each one of the lengthwise edges, said containment assembly corresponding to said rear waist region, or as an option, said first and second elastic belts extends laterally outwards from the said corresponding first and second extension ears; each one of said first and second elastic belts having a close edge joined to said rear region of the waist, or as an option, each one of the said first and second elastic belt having a close edge joined to the said corresponding first and second extension ears, and a distant edge laterally separated outwards from said closed edge, the gripping devices in said distant edge being connected, where said elastic belts includes a structure which includes a top nonwoven layer, a back nonwoven layer, and a layer of elastomer cords placed between said top and back nonwoven layers, jointly forming said elastic belts, which provide a maximum elasticity up to 500%, and where said material of the top and back nonwoven layers provides a characteristic of increased respirability.

BRIEF DESCRIPTION OF THE DRAWINGS

Since the specification concludes with the claims which set forth particularly and claim the topic, which is considered as part of this invention, it is believed that the invention will be better understood on the basis of the following description, which is taken together with a attached drawings in which similar designations are used to designate substantially identical elements, and in which:

FIG. 6A is a plan view of an alternate method of construction of the disposable diaper of FIG. 1A, in its flattened state, showing the extension ears connected to both rear waist part of the diaper and elastic belts.

FIGS. 7A–7E is a chart which shows the contraction values of the fastening system of this invention versus the fastening systems of the state of the art;

FIG. 8A–8E is a tension chart versus elongation of the fastening system of this invention.

DETAILED DESCRIPTION OF THE INVENTION

The components of this invention will be described herein in terms of their use in disposable absorbent articles according to one method; however, it should be understood that the potential for use of the invention is not limited to diapers.

As used herein, the term "absorbent article" refers to devices which absorb and contain body eliminations and, more specifically, refers to devices which are placed against or close to the user's body to absorb and contain the various wastes eliminated by the body. The term "disposable" is used herein to describe absorbent articles, which are not intended to be washed or otherwise restored or reused, as an absorbent article (that is, they are intended to be disposed of after a single use and, preferably, to be recycled, composed or otherwise placed in an environment friendly manner).

The term "respirability" as used herein, refers to describing absorbent articles which have a characteristic that occurs when the delaying medium (air or water steam) can traverse the membrane of the material at such rate as to maintain adequate balance with the intended final use. A "unitary" absorbent article refers to absorbent articles which are formed from separate parts joined together to form a coordinated entity, in such way as not to require separate handling of the parts, such as a support and separate lining. A preferred method of an absorbent article of this invention is the disposable absorbent article, diaper 20 shown in FIG. 1. As used herein, the term "diaper" refers to an absorbent article generally used by babies and incontinent individuals, which is used around the lower torso of the user. However, it should be understood that this invention can also be applied to other absorbent articles such as under shorts for the incontinent, underclothing for the incontinent, supports and linings for diapers, training pants and similar.

Figure 1:
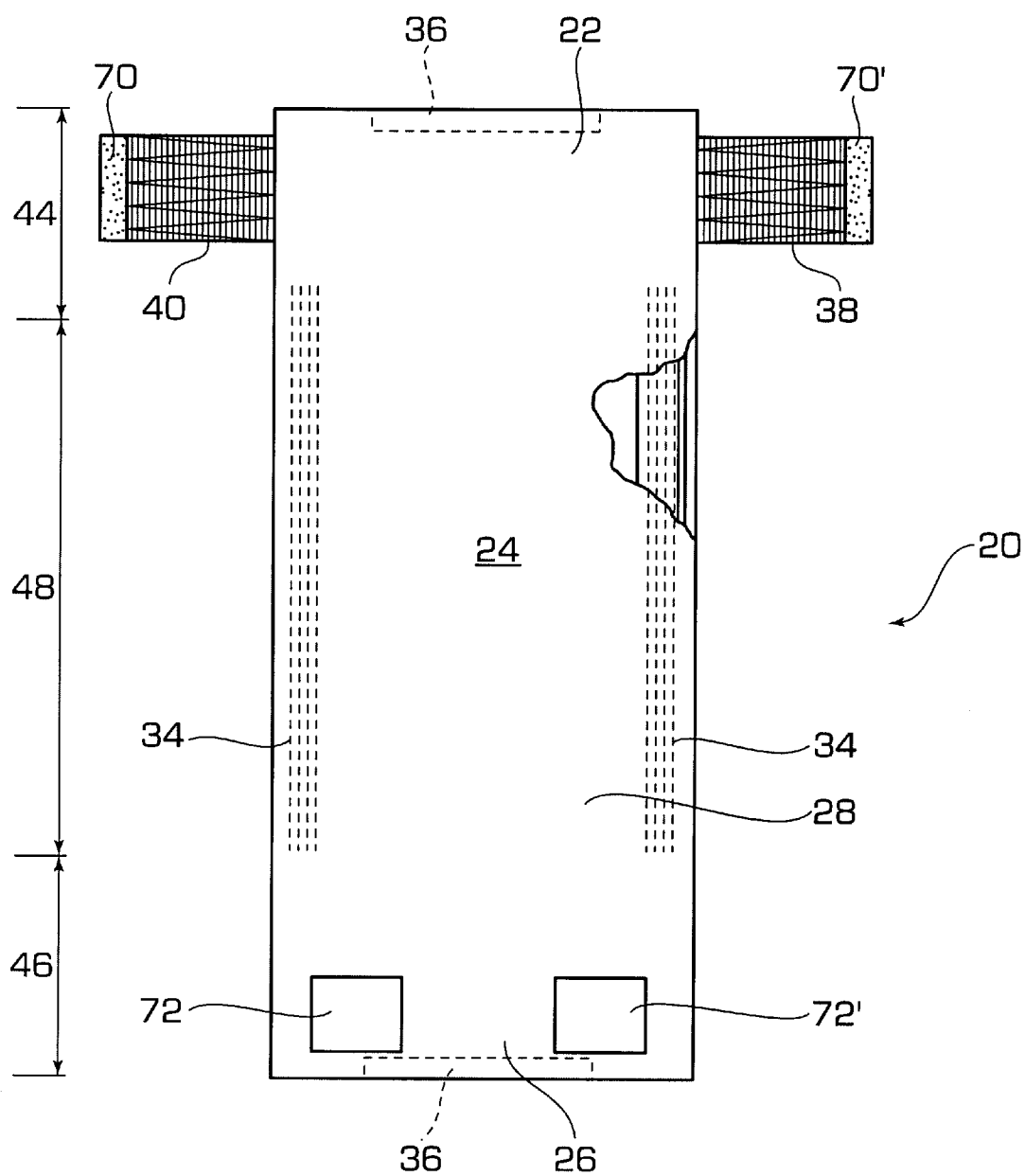
FIG. 1 is a plan view of a disposable diaper of this invention in its flattened condition, the absorbent diaper having cut portions to reveal the underlying structure; the outside of the diaper facing the viewer.
Figure 1A:
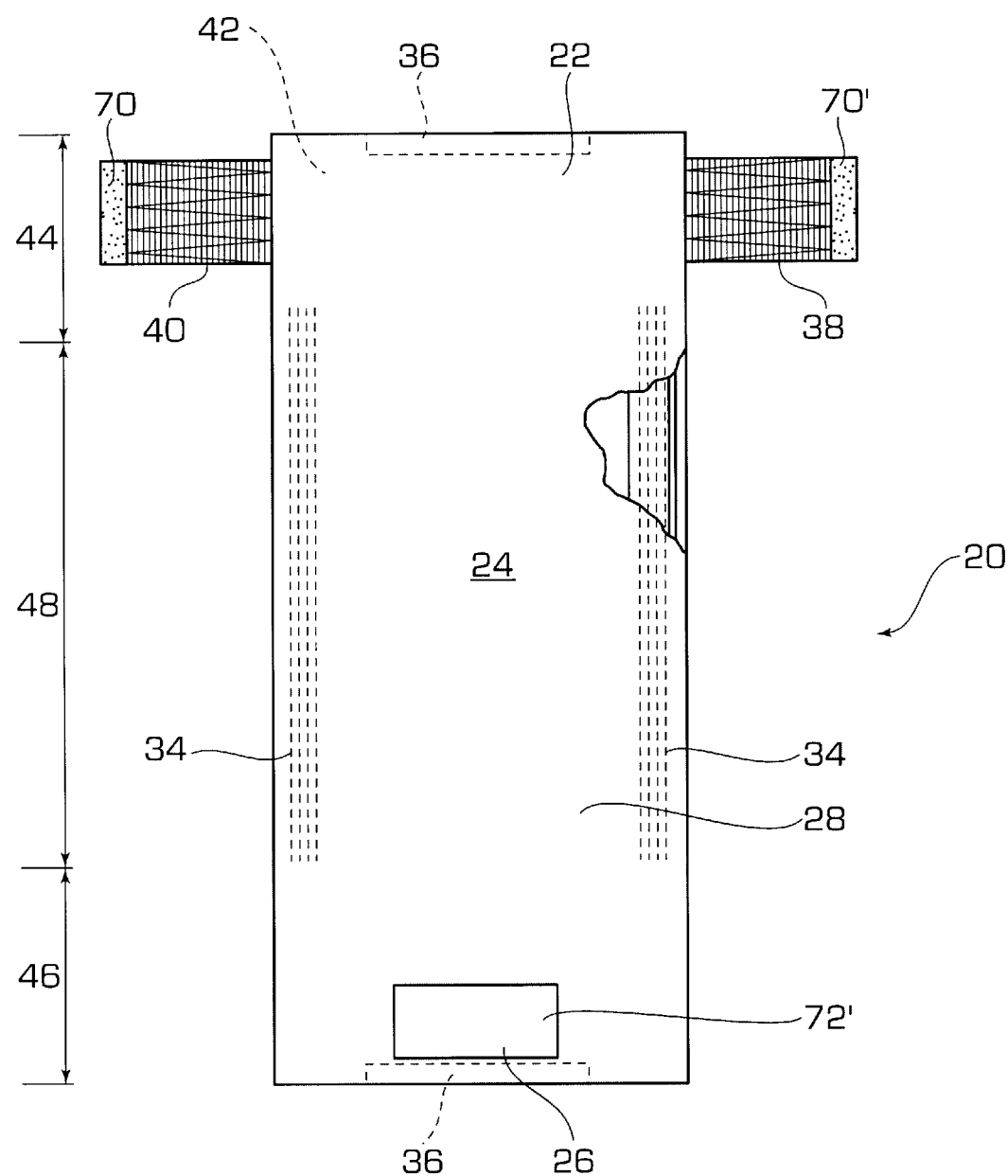
FIG. 1A is a plan view of a method of the disposable diaper contained in FIG. 1, showing a front landing, continuous band.

FIGS. 1 and 1A are plan views of diaper 20 of this invention in a non-contracted state, flat, extended (that is, with the elastic contraction induced downwards), the portions of the structure being cut to more clearly show the construction of diaper 20 and the portion of diaper 20 which looks away from the user, the outer area 22 facing the viewer. As shown in FIG. 1, diaper 20 includes preferably a containment assembly 24 which embodies a topsheet permeable to liquid 26; a backsheet impermeable to liquid 28 joined to the topsheet; and an absorbent core 30 placed between the topsheet 26 and the backsheet 28. Preferably the diaper also includes elastic leg devices 34; an elastic waist accessory 36; a first elastic belt 38; a second elastic belt 40; gripping devices 70; and a front landing band 72.

FIG. 1 shows the diaper 20 with an outer surface (viewed by the observer), an inner area 42 opposite the outer area 22, a rear waist region 44, a front waist region 46 opposite the rear waist region 44, a between-the-legs region 48 placed between the rear waist region 44 and the front waist region 46, and a periphery which is defined by the outer perimeter or edges of the diaper 20. The inner area 42 of the diaper 20 includes that portion of the diaper 20, which is located adjacent to the user's body during use (that is, the inner area 42 generally is formed by at least one portion of the topsheet 26 and the other components joined to the topsheet 26). The outer area 22 includes that portion of the diaper 20, which is away from the body of the user (that is, the outer surface 22 generally is formed by at least one portion of the backsheet 28 and the other components joined to the backsheet 28). As used herein, the term "connected" covers configurations, by which one element is directly adhered to the other element fastening the element directly to the other element, and configurations whereby the element is indirectly connected to the other element fastening the element to the member(s), which in turn are fastened to the other element. The rear waist region 44 and the front waist region 46 extend from the extreme edges of the periphery toward the area between the legs 48.

FIG. 1 shows the containment assembly 24 of the diaper 20 and includes the principal body (base) of the diaper 20. The containment assembly 24 includes at least one absorbent core 30 and preferably one layer of outer covering which includes the topsheet 26 and the backsheet 28. When the absorbent article includes a separate support and a lining the containment assembly 24 generally includes the support and the lining (that is, the containment assembly 24 includes one or more layers of material to define the support, while the lining includes an absorbent mixed material, such as a topsheet, a backsheet and an absorbent core). For unitary absorbent articles, the containment assembly 24 includes the principal structure of the diaper with other added characteristics to form the mixed diaper structure. This way, the containment assembly 24 for the diaper 20 generally includes the topsheet 26, the backsheet 28 and the absorbent core 30.

Figure 2:
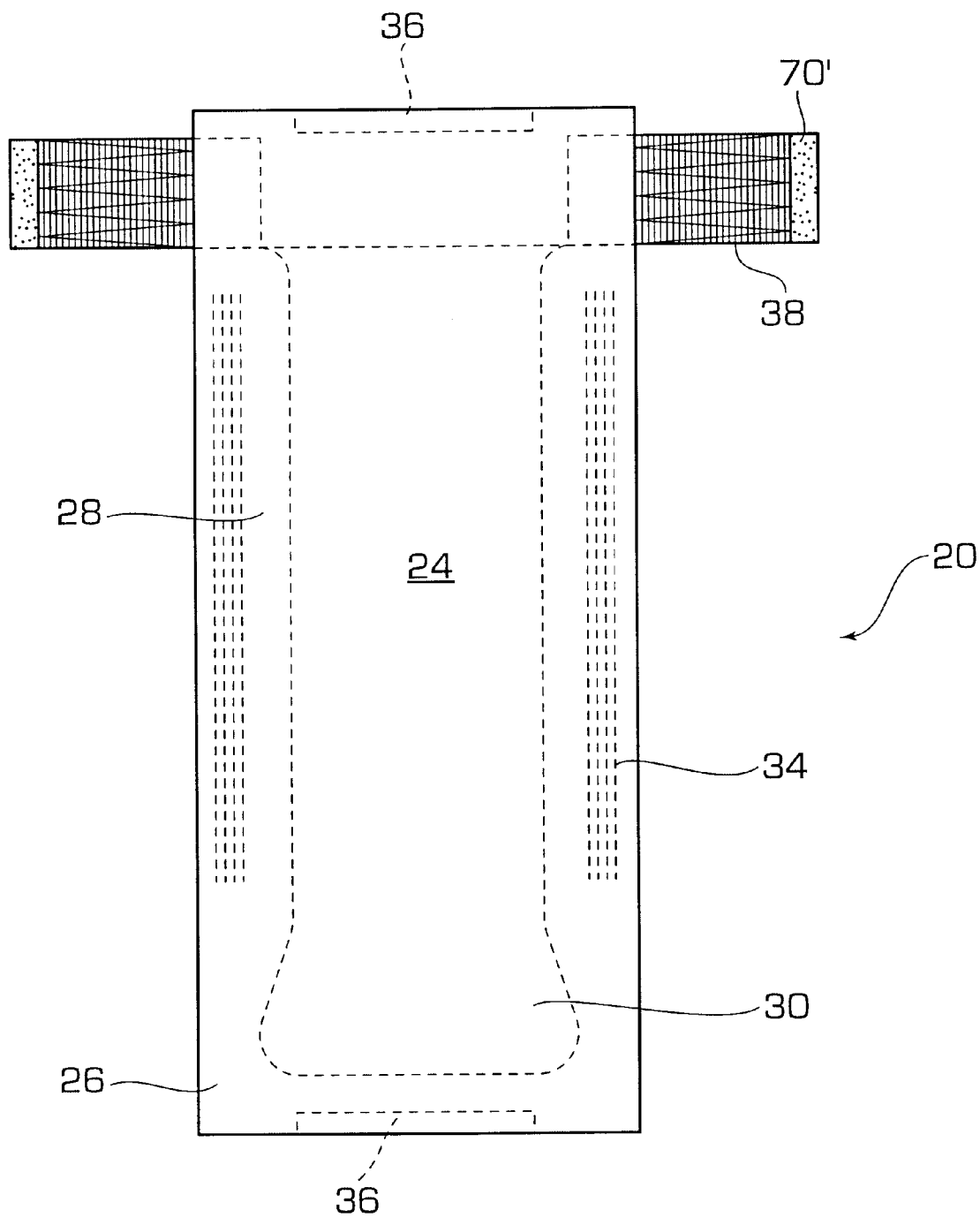
FIG. 2 is a plan view of the disposable diaper of this invention in its flattened state, the inside surface of the diaper facing the viewer.
Figure 2A:
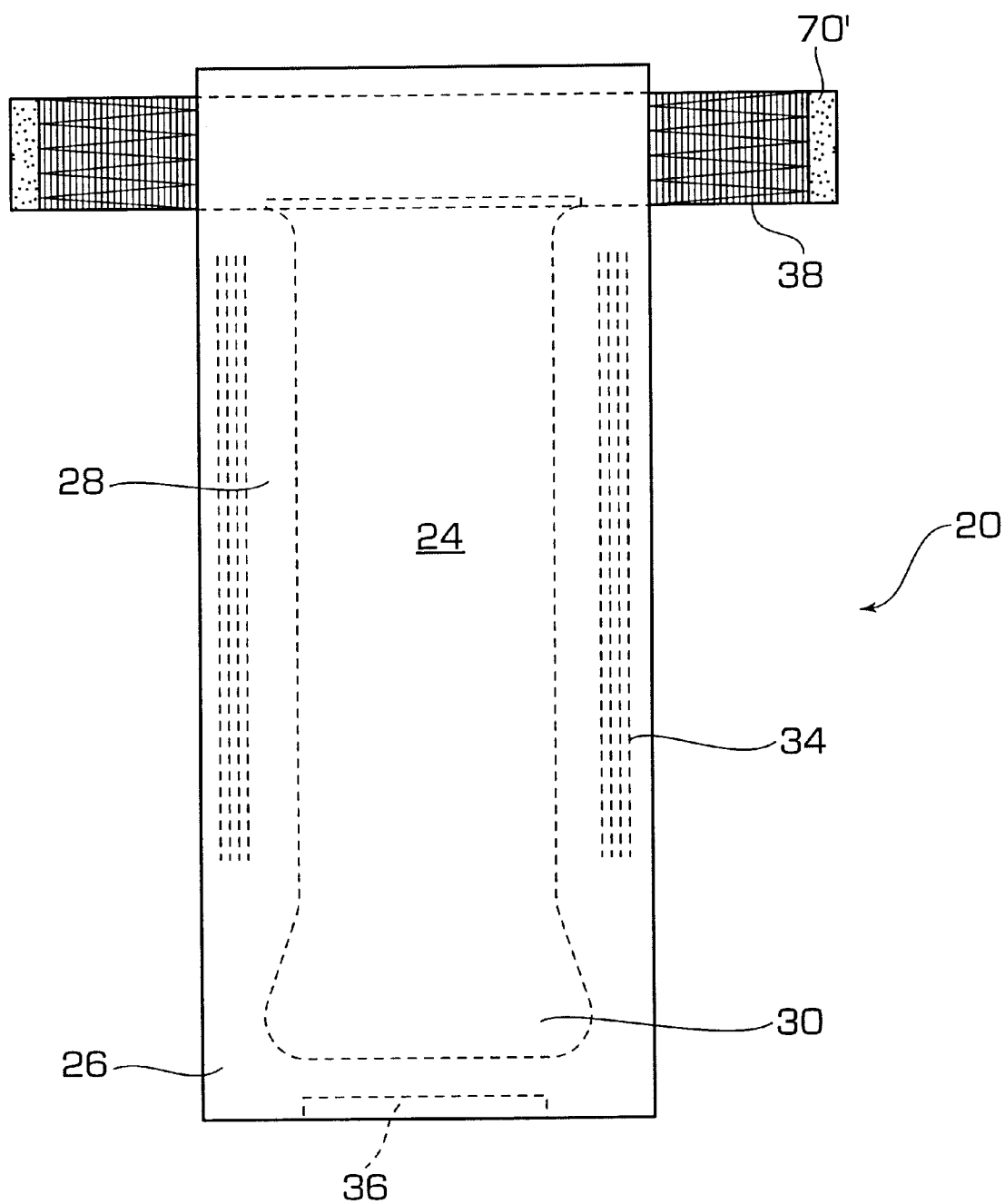
FIG. 2A is a plan view of a method of the disposable diaper contained in FIG. 2, showing a lateral elastic belt connected to a nonwoven film band at the center; the inside of the diaper facing the viewer.

FIGS. 2 and 2A shows a preferred method on the containment assembly 24, in which the topsheet 26 and the backsheet 28 have length and width dimensions generally greater than those of the absorbent core 30. The topsheet 26 and the backsheet 28 extend beyond the edges of the absorbent core 30 to thereby form the periphery of the diaper 20. Since the topsheet 26, the backsheet 28 and the absorbent core 30 can be assembled in a variety of well known configurations; some of the configurations of illustrative containment assemblies are described generally in U.S. Pat. No. 3,860,003 and U.S. Pat. No. 5,151,092, each of which is incorporated herein by reference.

The absorbent core 30 can be any absorbent member, which is generally compressible, comfortable and not irritating to the user's skin, and capable of absorbing and retaining liquids, such as urine and other body eliminations. The absorbent core 30 can be manufactured in a wide variety of sizes and forms (v.gr. rectangular, in the shape of a sand clock, in a "T" shape, asymmetric, etc.), and of a wide variety of liquid-absorbing materials commonly used in disposable diapers and other absorbent articles, such as crushed wood pulp (which is generally called air felt) and/or alpha cellulose pulp. They include examples of other absorbent materials, curled cellulose cotton waste; fusion-blown polymers including coform; hardened cellulose fibers, chemically modified or intertwined; woven including woven wrappings and woven laminated units; absorbent foams; absorbent sponges, super absorbent polymers; absorbent gel materials; or any equivalent material or combination of materials.

The configuration and construction of the absorbent core 30 may vary (v.gr., the absorbent core can have variable gauging zones, a hydrophilic gradient, a super absorbent gradient, or areas of average low density and weight acquisition on the basis of the lower average; or it can include one or more layers or structures). In addition, the size and absorbent capacity of the absorbent core 30 may also be varied to satisfy the users, which range from babies to adults. Nevertheless, the total absorbent capacity of the absorbent core 30 may be compatible with the design load and the intended use of the diaper 20.

The absorbent core may also include an inner layer of distribution (v.gr. a sublayer), such as a sheet of tissue paper to improve the cutting characteristics of the core during the manufacturing process. In addition, said distribution layer is placed on the lower part of the absorbent core, in order to improve the acquisition and distribution of fluids over the length of the absorbent core. Said fluid distribution layer is placed between the absorbent core and the backsheet, and preferably the latter is connected by means of heat-fused adhesives. This way, the body fluids absorb through the absorbent core and before reaching the outer sheet, will make contact with the internal liquid distribution layer, where the distribution of the fluid will improve along the length and width of the lower part of the absorbent core, maintaining the upper part of the absorbent core drier. This internal fluid distribution layer is included in order to avoid humidity reaching the user's skin. In addition, the absorbent article may embody a second sheet for liquid distribution composed of different materials, such as for example polypropylene, a yarn interlaced material and heat interlaced material. Said sheet would be placed between the topsheet 24 and the absorbent core 30.

Backsheet 28 is placed adjacent to the surface facing the absorbent core garment 30 and preferably joined to it by connecting devices (not shown) such as those well known in the art. For example, the backsheet 28 can be fastened to the absorbent core 30 by a uniform, continual adhesive layer, or a placement of adhesive lines, spirals or separated points. There are in the art various adhesives with the required characteristics, such as the one manufactured by H. B. Fuller Company, St. Paul, Minn. and sold as HL-1258. An example of adequate connecting devices comprised by an open-pattern net of adhesive filaments is described in U.S. Pat. No. 4,573,986 entitled "Disposable Waste Containment Garment" issued to Minetola and others on Mar. 4, 1986. Other adequate connecting media which are comprised of various lines of rolled adhesive filaments in a spiral pattern is illustrated with the apparatus and methods displayed in U.S. Pat. No. 3,911,173 issued to Sprague, Jr. on Oct. 7, 1975; U.S. Pat. No. 4,785,996 issued to Ziecker and others on Nov. 22, 1988, and U.S. Pat. No. 4,842,666 issued to Werenicz on Jun. 27, 1989. Each of these patents is incorporated herein by reference. Alternatively, the connecting media can include heat-connecting, pressure-connecting, ultrasonic connecting, dynamic mechanical connecting or any other connecting media or combinations of this connecting media as known in the art.

Backsheet 28 is impermeable to liquids (v.gr., urine) and preferably is manufactured from a thin plastic film, although other materials impermeable to liquids, flexible, may be used, as well as materials derived from natural resins. As used herein, the term "flexible" refers to materials which are comfortable and easily adapted to the form and shapes of the human body. Backsheet 28 prevents the eliminations that are absorbed and contained in the absorbent core 30 from moistening the articles that are in contact with the diaper 20, such as underclothing; however, backsheet 28 can allow steam from the absorbent core 30 to escape (that is, that it be respirable). This way, the backsheet 28 preferably comprises polymer films of woven or nonwoven material, such as thermoplastic polyethylene or polypropylene film, or mixed materials, such as a film-coated nonwoven material. An adequate backsheet 28 is a sheet made of polyethylene.

The topsheet 24 is comfortable, soft to the touch and does not irritate the user's skin. In addition, the topsheet 24 is preferably permeable to liquid, allowing liquids (v.gr. urine) to easily penetrate through its thickness. An adequate topsheet 24 can be manufactured from a wide variety of materials, such as porous foams; reticulated foams; plastic films with opening; or woven or nonwoven natural fiber bands (v.gr. wood or cotton fibers), synthetic fibers (v.gr. polyesther or polypropylene fibers), or a combination of natural and synthetic fibers.

The backsheet is made preferably from a hydrophobic material to isolate the user's clothing from the liquids which have passed through the topsheet 24 and which are contained in the absorbent core 30; that is, to avoid moistening of the clothing.

Preferably, diaper 20 also comprises elastic leg devices 34 to provide an improved containment of liquids and other body eliminations. Each leg elastic medium 34 may include different methods to reduce the leaking of body eliminations in the leg region; each leg elastic medium 34 preferably includes elastomer threads which are tied by media well known in the art, such as pressure-sensitive adhesives. The elastic leg devices are placed close to the lengthwise edges of the containment assembly, to form a seal between the area between the legs 48, thus forming a barrier to avoid the body liquids escaping from the containment assembly through the space formed during the movement of the user's muscles, and spotting the user's underclothing.

Elastic belts 38 and 40 wrap around part of the user's waist when the diaper 20 is adjusted to the user. When the diaper is adjusted to the user in the conventional configuration, elastic belts 38 and 40 extend from the rear waist region 44 of the diaper 20, or in other typical application, from the distant edge 98 of the corresponding extension ear 120, around the user's hips towards the front waist region 46 of the diaper, where the elastic belts 38 and 40 grip to the front waist region 46, forming the fastening of the diaper's belt.

Each elastic belt is preferably placed close to one of the lengthwise edges of the containment assembly 22, preferably in the rear waist region 44; or connected to one of the extension ear 120 of the diaper 20, as observed in FIG. 6A. As observed in FIGS. 1 to 2A, each one of the elastic belts 38 and 40 has a close edge and a distant edge. For example, in FIGS. 3 to 5, the first elastic belt 38 has a close end 66 placed adjacent to one of the lengthwise edges of the containment assembly 22 in the rear waist region 44 of the diaper 20, or in other typical application, the close end 66 is placed adjacent to one of the distant edges 98 of the extension ear 120, as observed in FIG. 6A, and a distant edge 68 laterally separated outwards toward the close end 66. In a preferred method of this invention, the elastic belts 38 and 40 can be elastically extended laterally to provide a more comfortable and shaped adjustment. (As used herein, the term "elastically extended" refers to materials which extend in at least one direction when force is applied and return to their approximate original dimensions after the force is removed. The elastic belts which can be elastically extended also provide a more effective application of the diaper, since even if the person adjusts the diaper to the user asymmetrically, the diaper will adjust itself during use to obtain an improved adjustment. Moreover, the elastic belts which can be extended elastically provide an improved dynamic adjustment around the user's waist, reducing the possibility of becoming loose or opening, and maintaining the diaper adjustment throughout the time of use.

The elastic belts 38 and 40 are soft to the touch and can have a number of different sizes, forms and configurations. The exact length, width and thickness of the elastic belts 38 and 40, and the extension ears 120, will vary depending on the sizes of the intended user. In the preferred methods of this invention, at least part of the extension ear or elastic belt is disposed between the topsheet and the backsheet of the absorbent diaper, and joined to them by heat-fusion adhesive, by ultrasound or pressure. The sizes of the elastic belts are preferably taken when the elastic belts are under some tension instead of when the elastic belts are in their relaxed state. This ensures that the elastic belts will provide the diaper 20 with the advantages mentioned above. The elastic belts include a separate element or several elements joined to diaper 20, which can be joined by any medium known in the art. Examples of adequate connecting media include adhesive connecting, heat connecting, pressure connecting, ultrasonic connecting, dynamic mechanical connecting or a combination of any of these media or any other media known in the art.

Figure 4:
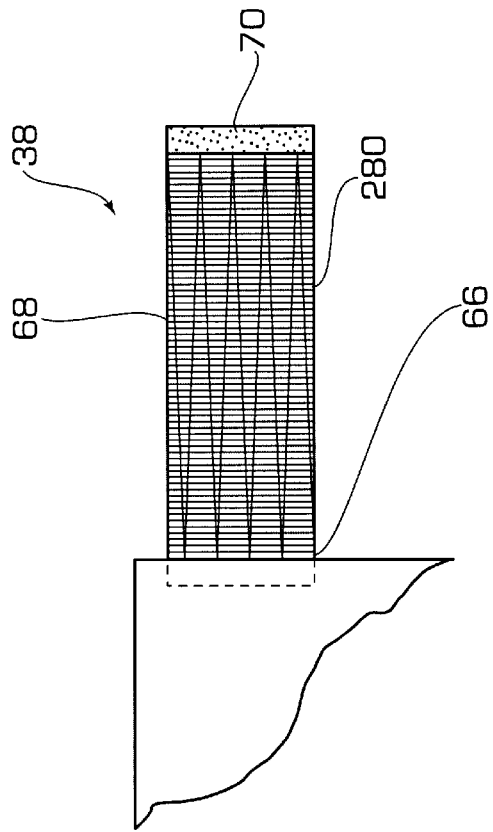
FIG. 4 is an amplified sectional view showing the elastic belt in its forced or tensioned position.
Figure 3:
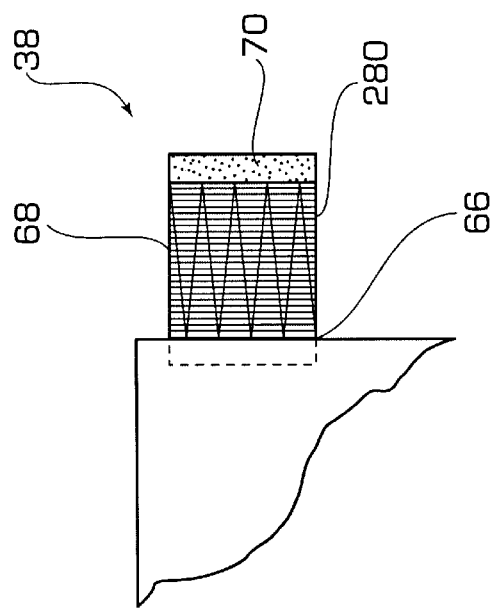
FIG. 3 is an amplified sectional view which shows the elastic belt in its relaxed position.

A material that can be extended elastically which has been found to be particularly adequate for use in the elastic tying belts is composed of two layers of nonwoven portions of polypropylene in different gram levels and configurations. In the intermediate portion between these two layers is a portion of elastomer threads 80, in zig zag, in different decitex or deniers, which have elasticity characteristics up to 500%. The direction of the threads or elastomer guides 80 in zig zag is such that their elongation characteristic is provided in the same stretching direction at the time of tying the elastic tie belts at the front part of the diaper; that is, the lengthwise sense of the elastic elements is in a perpendicular or cross-directional form with respect to the topsheet and backsheet of the diaper. The threads 280 (as shown in FIGS. 3 and 4) in their zig zag course are imbibed in adhesive or heat-fusion material so that the elastomer threads fasten to the polypropylene nonwoven portion of the layers, jointly forming an element in the form of an elastic band or belts which perfectly adapt to the shape of the user's waist. An important characteristic of this invention is the respirability of the elastic belts, because the layers that enclose the elastomer threads, being made of nonwoven polypropylene are porous and thus permeable, allowing the passing of air and gases. In contrast, the gripping belts or elements of the state of the art are elastomer laminations which are impermeable to the passing of gases.

Figure 5:
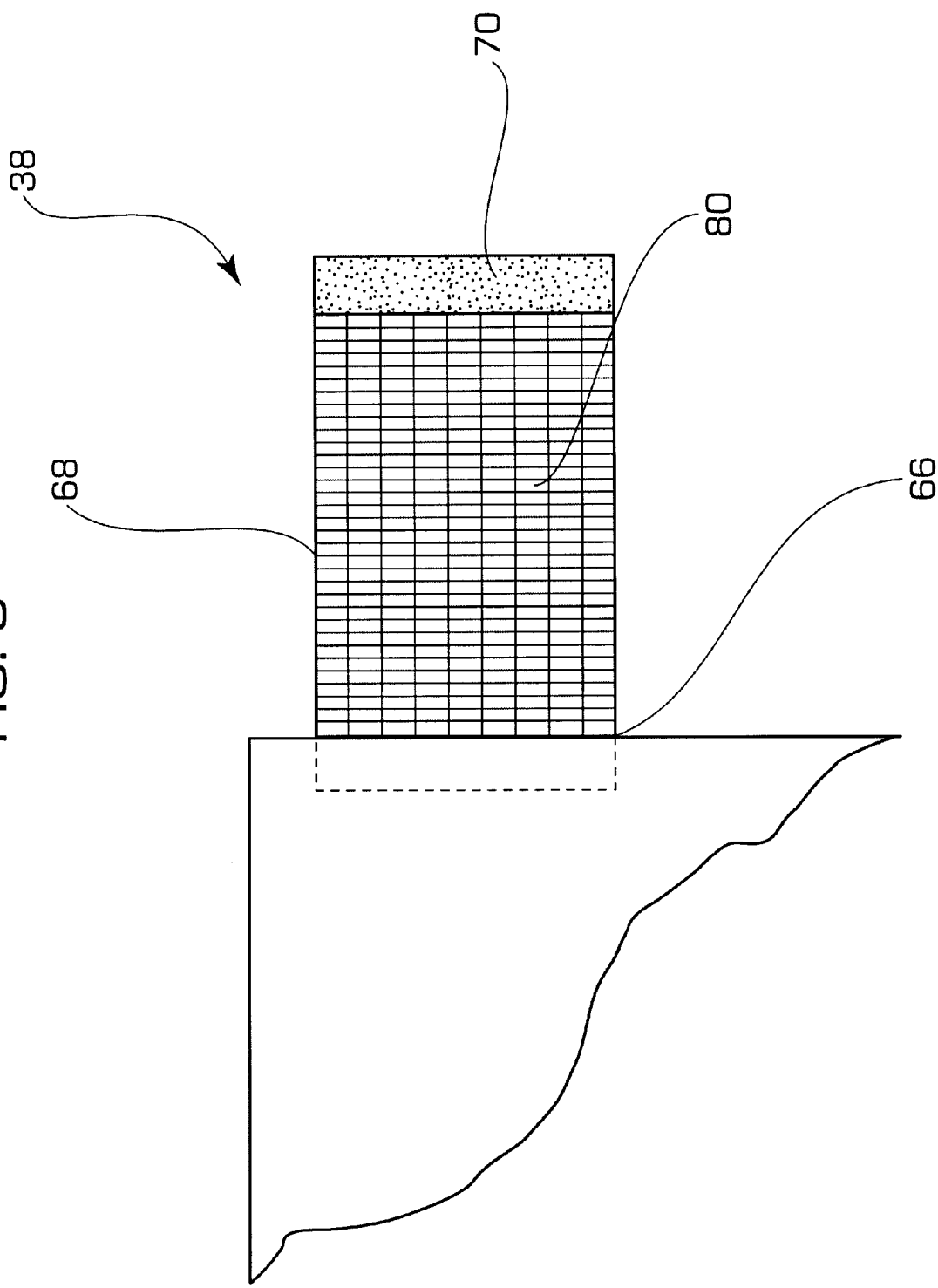
FIG. 5 is an amplified sectional view of an alternate method of an elastic belt in its forced or stretched position.

An alternative method of elastomer threads of this invention, as shown in FIG. 5, comprises a portion of elastomer threads 80 which are constructed in an on-line configuration; that is, in the direction towards which the stretching tension will be applied. In both dispositions of the elastomer threads within the elastic belts (see FIGS. 3 to 5) an elasticity of approximately 300% is provided, with a 90% recovery percentage after each tension effort, that is, after stretching. These properties provide additional characteristics to elastic belts; that is, they do not lose their shape or their retraction force.

In addition, the embodiment of the above elements in the absorbent diaper of this invention will allow for savings of up to 49% of the addition of other materials, such as the topsheet and the backsheet, which reduces proportionally the application of adhesives to connect them.

The tying system (as shown in FIGS. 1 to 5) can comprise any connecting medium known in the art, including pressure-sensitive adhesive, cohesive materials, mechanical fasteners, hook and loop fasteners, or any combination thereof, or any other connecting medium known in the art. In a preferred method of this invention, the tying system comprises hook and loop type fasteners. As used herein, the term "hook and loop fasteners" refers to fastener media which include a "hook" component 70 (hereinafter called a "coupling component") and a complementary knot component 72 (hereinafter called a "landing component"). The term "hook" is used to designate a material which has coupling elements. This way, the fastening material of hook 70 can also be called the male fastener. It should be understood that the use of the term "hook" should not be limited in the sense that the coupling element can comprise any forms known in the art, since these are adapted to couple with a complementary arrival component.

The landing component 72,72' (as shown in FIGS. 1 to 2A) preferably comprises a fastening element that can couple with the hook component 70,70'. This way, the landing component 72,72' can be manufactured from a wide variety of materials and configurations capable of safely coupling the hook component. The functioning of the pressure adhesive-sensitive tying system or the hook and loop type will not be described, since it is well known to those with average know how in the subject matter.

Figure 6:
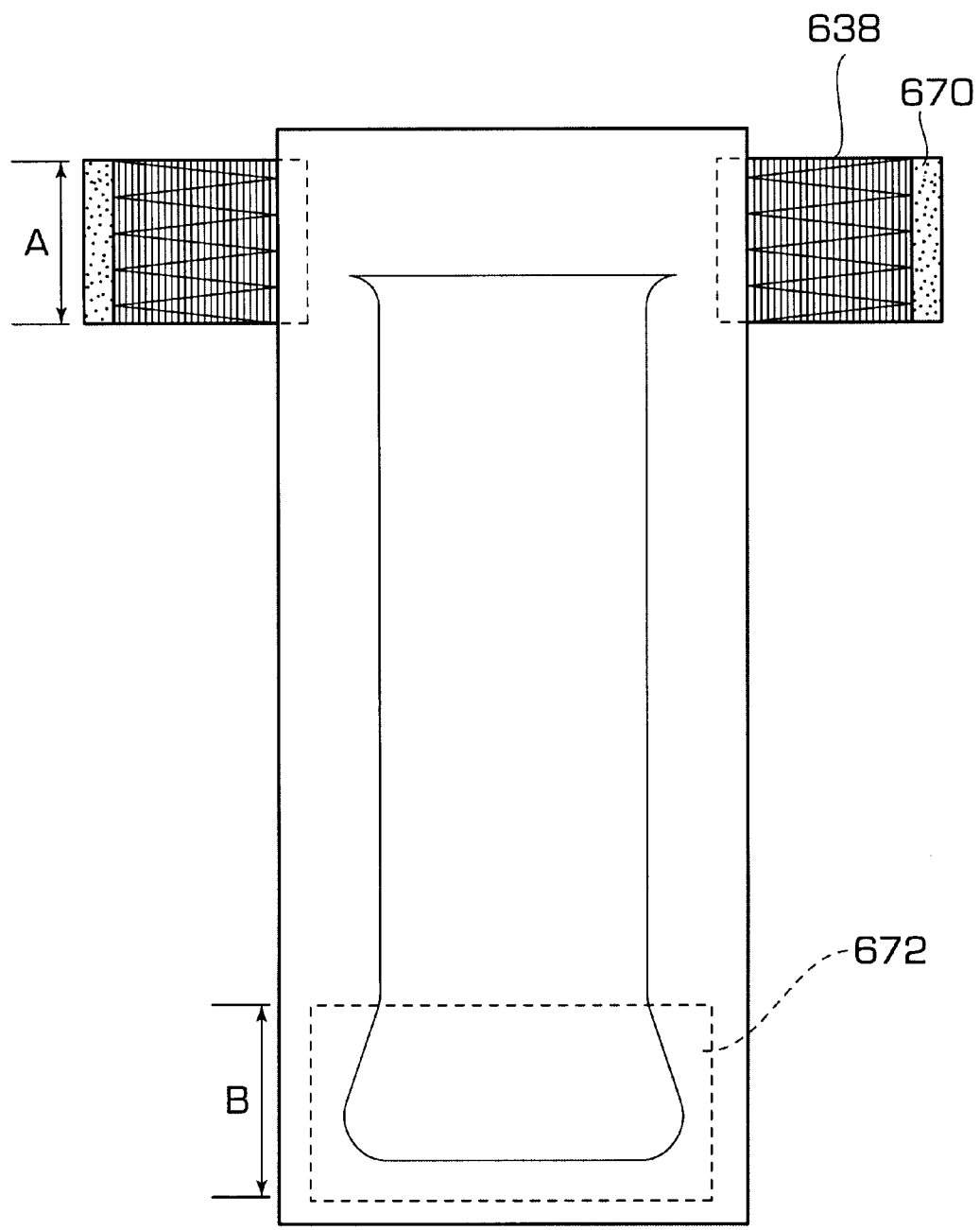
FIG. 6 is a plan view of an alternate method of the disposable diaper of FIG. 1A, in its flattened state, showing wider elastic belt and front landing band.
Figure 7B:
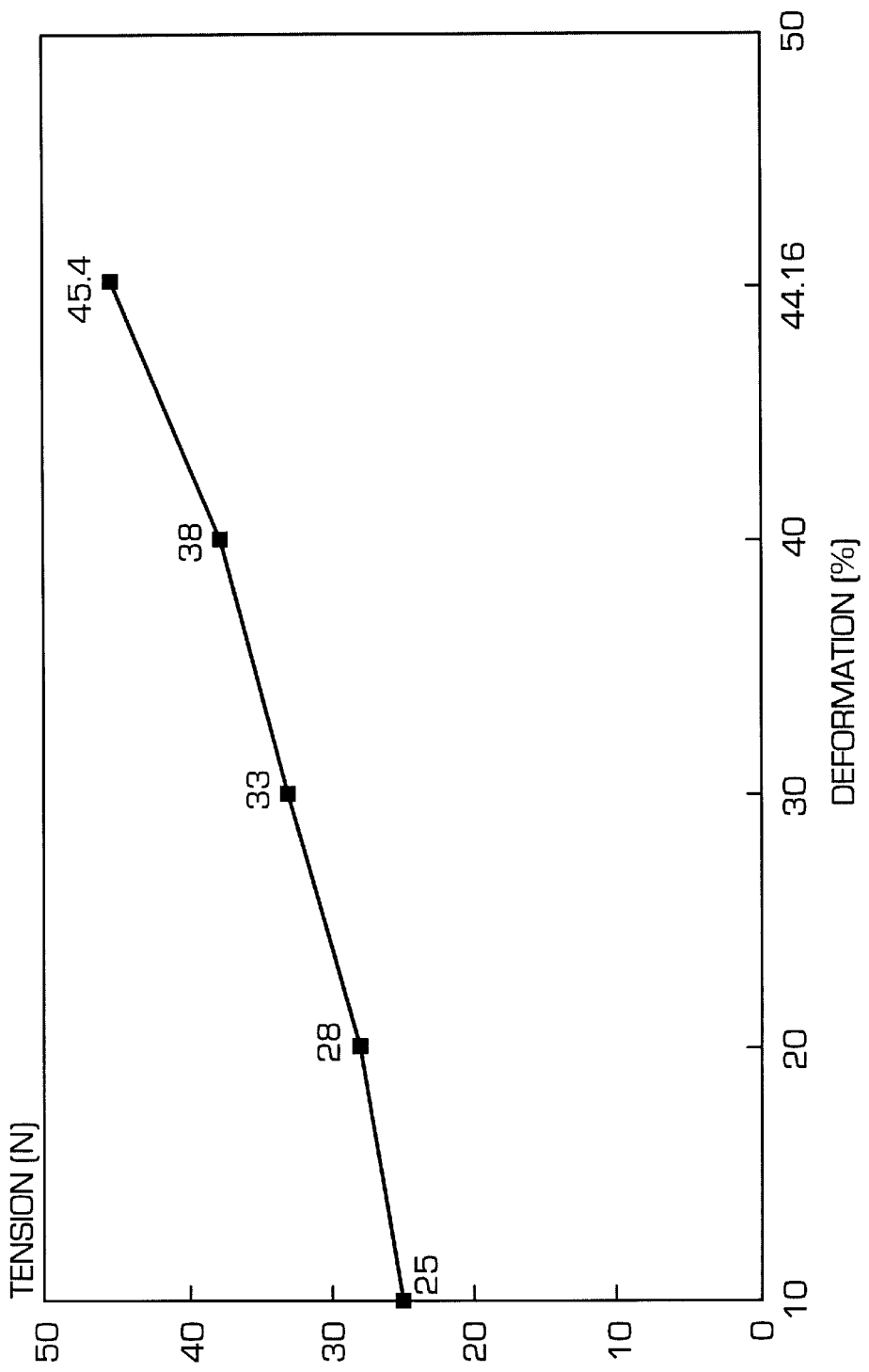
Figure 7E:
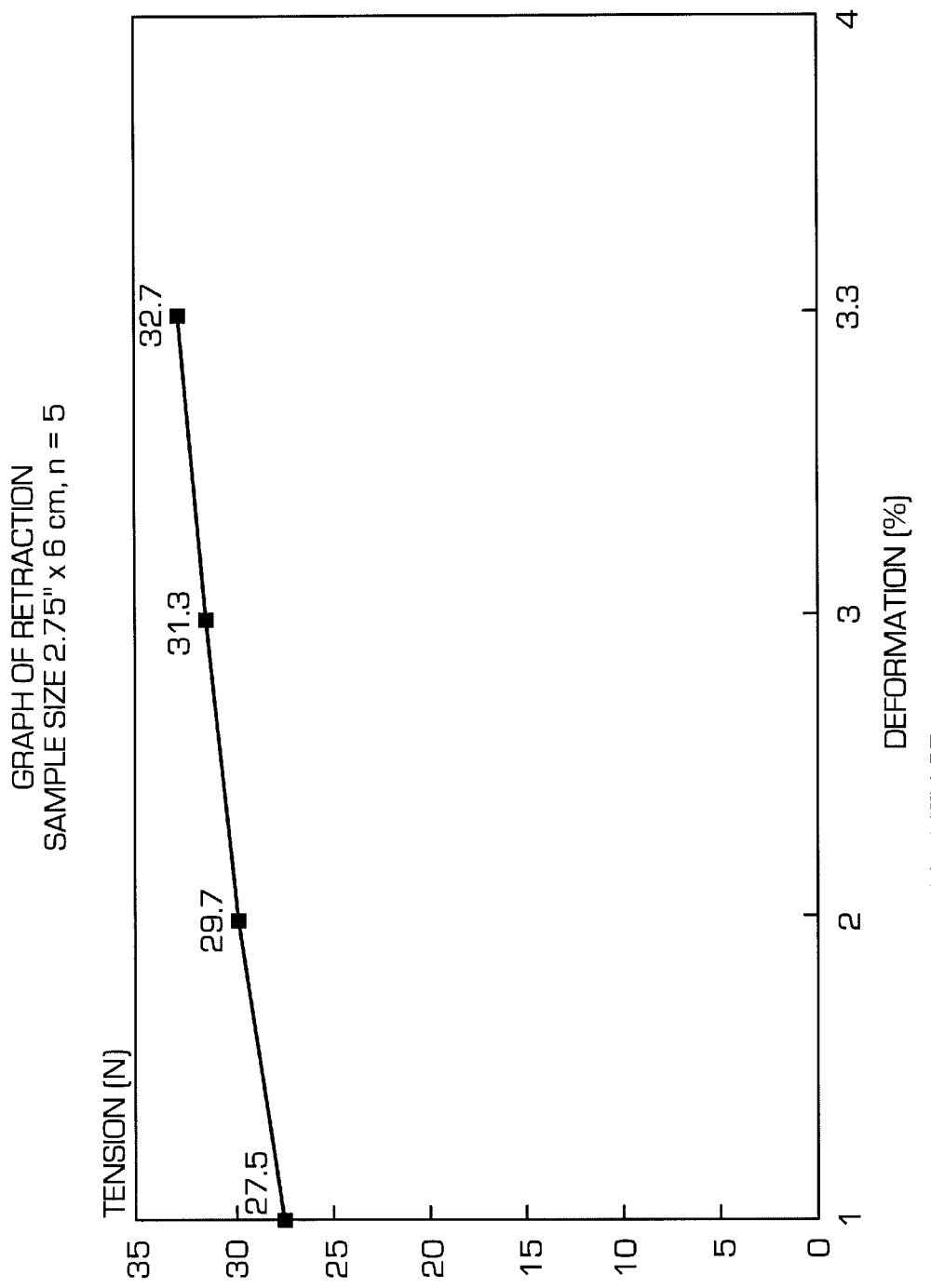
Figure 8A:
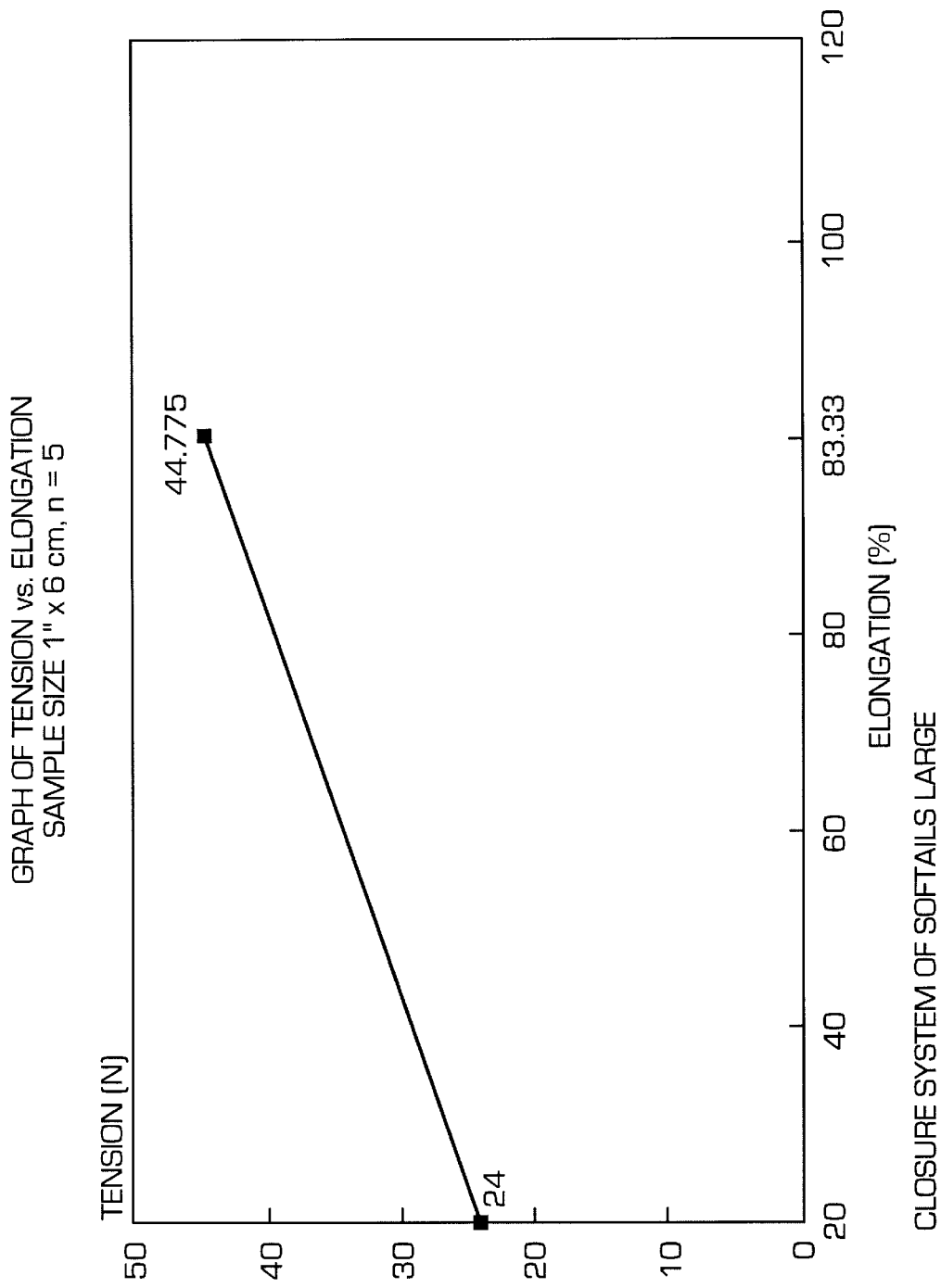
Figure 8D:
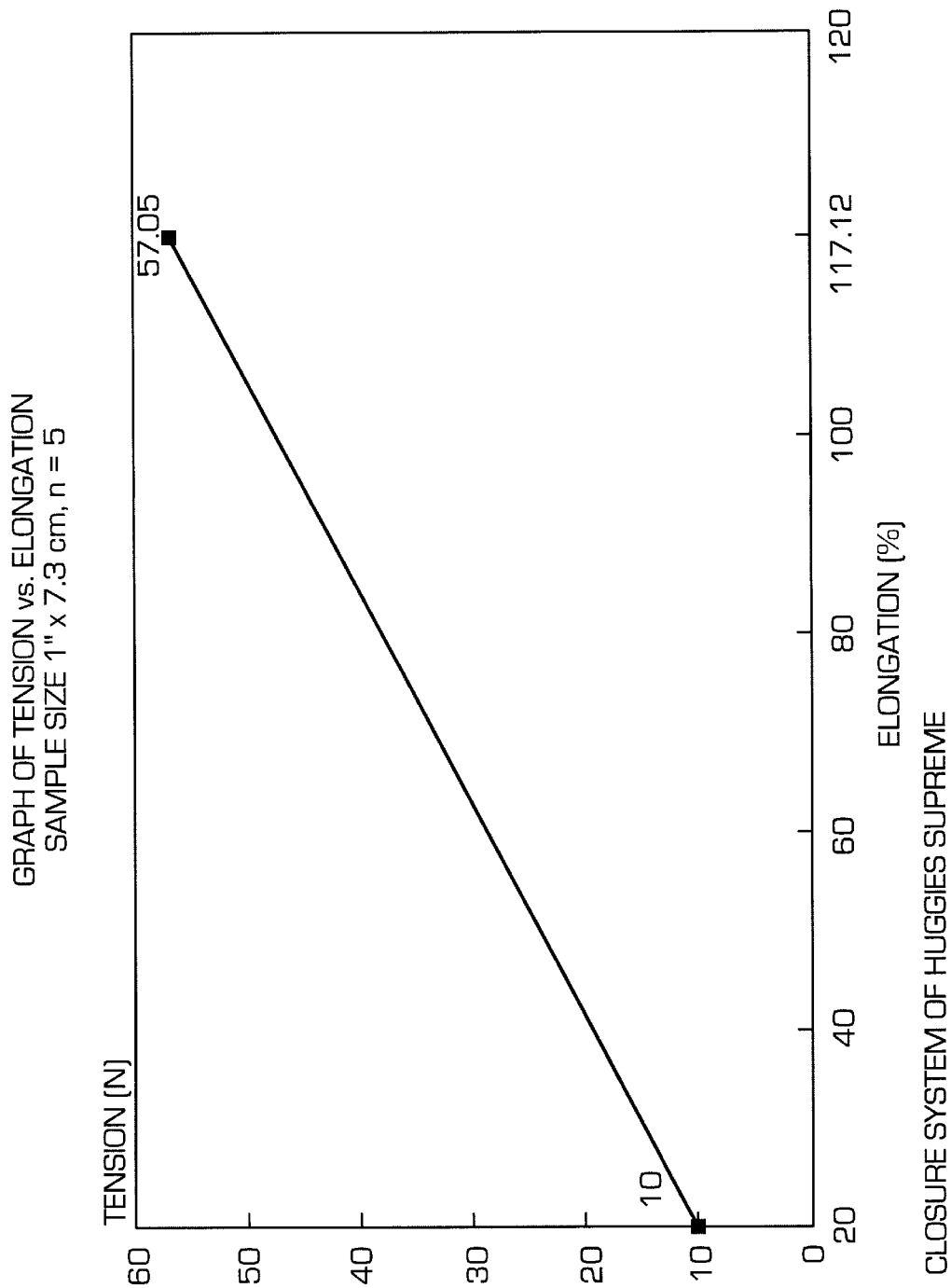

Now referring to FIG. 6, it shows an alternative method of the elastic belt and the front landing band, which are wider. This type of belt 638 and landing band 672 are wider, to provide a configuration of a diaper of the support brief type in order to improve the support and adjustment area when the disposable article is used.

In a particularly preferred method of this invention, the diaper can be used as training pants. For example, the diaper can be constructed in either the conventional configuration or assembled to form training pants before adjusting the diaper to the user. Then the user pulls the diaper upwards and over his gluteal region, where it remains in place around the user's waist by the internal force provided by the elastic belts. In this configuration, the diaper can be removed by pulling it downwards and out from the user without releasing the fastening system or releasing the fastening system and removing the diaper from the user's waist. Alternatively, the diaper can be constructed and adjusted to the user as described herein with respect to the configuration of the conventional diaper or training pants and can be removed by pulling the diaper downwards over the user's gluteal area and from the user without releasing the fastening system. Consequently, the user of the diaper is provided with additional options of how to adjust and/or remove the user's diaper. This type of diaper is particularly attractive as training pants, since it combines the sensation of underpants with the advantages mentioned herein with respect to the ease of inspecting whether or not the diaper is dirty and its removal, releasing the fastening system.

Test Methods

Measurement of maximum elongation and deformation.

To measure the maximum elongation and deformation of the elastic belts of this invention, a Longitudinal Tension Digital Meter was used, model Accuforce III, manufactured by Mansfield & Green Division, and marketed under the registered trademark Ametek, and a centimeter graduated linear scale (scale 0–50 cm).

In conducting this test, disposable diapers with anatomical fastening elements were used, such as those manufactured under the registered trademark Kleen-Bebe (Kimberly-Clark Corporation), Huggies Supreme (Kimberly-Clark Corporation), Pampers Premium (The Procter & Gamble Co.), Softails Large (Absormex, S.A. de C.V.), and the diaper with the fastening system of this invention.

Samples were prepared by cutting approximately 4 cm from the topsheet of the elastic belts starting from the end of the portion anchored between the topsheet and the backsheet of the absorbent diaper. The purpose of using only this sample which comprises the fastening system is to obtain maximum elongation and deformation characteristics when the samples, which is the fastening element of the diaper's fastening system are submitted to extreme elongational tension conditions; that is, toward the tying element.

According to the foregoing, one end of the sample is placed (v.gr., the portion which is anchored to the topsheet and backsheet) in the grip, which will act as the point of support of the tension meter, and it is closed by squeezing to a point where the sample does not slip from the grip. The other extreme of the sample (v.gr., the portion of the fastener) is placed within the jaw of the mechanism which will perform the stretching and the tension, contrariwise to the position of the tension meter's jaw. Then the separation between the jaws is gauged in such way that the sample is submitted to no stretching (zero tension) at the starting point of the tension course. The sample is measured before submitting it to stretching, taking as a point of reference the side of the element placed in the jaw of the tension meter up to the contrary jaw, to the point where the union of the release and fastening tie ends (in the case of pressure-sensitive adhesive ties), or up to the point where the tie or hook begins (in the case of mechanical ties).

The reading of the tension meter is gauged to indicate zero when the test is launched. The stretch velocity of the equipment is adjusted to 2.5 inches/minute. The distance reference is taken of the scale graduated in centimeters, taking as the departure points the initial position of the jaw of the longitudinal advance mechanism. The stretching mechanism is started up, whereby tension readings are registered in the tension meter display when complete distances are reached (for example every 3 cm). The measurement is conducted under normal laboratory conditions. The term "deformation" as utilized herein, refers to the point at which any of the elements comprising the sample (that is, the portion of the fastening system anchored between the topsheet and backsheet, the elastic element and the tying system) undergoes an unrecoverable elongation of its original dimensions. The tension at which the formation occurs in any of the components of the sample is registered. The test continues up to the point at which any of the components of the sample breaks, registering the tension at which this occurs. The data obtained from the samples are described in FIGS. 7A–7E and 8A–8E, where elongation and deformation percentages are compared with respect to tensions applied to them.

Conclusions

The products comprised in traditional fastening systems without elastic elements (such as those marketed by The Procter & Gamble Co. under the registered trademark "Pampers Fases" and Mabesa, S.A. de C.V. under the brand "Chicolor") present a low elongation percentage without undergoing deformation, the elongation capacity is increased when the sample begins to show deformations which, nevertheless, are irrecoverable. In this type of fastening system the point of rupture generally occurs in the material where the tying element is fastened; that is in the nonwoven or polyethylene portion.

With respect to fastening systems which embody elastic elements in the fastening system, such as diapers manufactured under the registered trademarks Pampers Premium and/or Huggies Supreme, they present significant elongation characteristics. Nevertheless, the elasticity characteristic of these systems is supported, to a great extent, by the elasticity of the topsheet itself (polypropylene film) and the backsheet of the absorbent diaper; that is, the fastening element (shown in FIG. 4) does not posses a considerable elasticity characteristic of itself, but rather the composite is what provides said characteristic.

As observed in FIGS. 7 and 8, the respirable elastic belt of this invention shows superior elasticity characteristics (up to 280%) with minimum deformation (up to 3.3%). Another important aspect of this invention lies in the fact that the respirable elastic tying belt is the one which demands the least tension to provide stated elongation characteristics, and as a direct result, provides greater comfort and anatomical adjustment around the user's waist, thereby avoiding the probability of causing blotches and skin flaking on the baby or bed-ridden adult, due to super tension on adjusting the diaper. It should be mentioned that the material of the sample of this invention used during the tests contained Lycra® 620 denier (620 grams in 9 Km of yarn). Nevertheless, the elastic tying belt of this invention can use other elastic elements such as natural or synthetic rubber, latex, to improve the elongation characteristics.

Since specific methods of this invention have been illustrated and described, it will be obvious for experts in the art to make various changes and modifications without deviating from the spirit and scope of the invention. Consequently, it is intended, in the attached claims, to cover said changes and modifications that fall within the scope of this invention.

What is claimed is:

1. An absorbent article comprising:
   a containment assembly which has an outer surface facing away from a user, an inner surface facing the user, a rear waist region, a front waist region and a between-the-legs region between said front and rear waist regions, said between-the-legs region having a pair of lengthwise edges, said containment assembly comprising a topsheet permeable to liquid, a backsheet impermeable to liquid, and an absorbent core placed between the topsheet and backsheet;
   elastic leg devices disposed in the between-legs region of said containment assembly;
   first and second elastic belts placed in the rear waist region of said containment assembly;
   at least one landing band placed in the front waist region of said containment assembly; and
   gripping devices to ensure the first and second elastic belts are capable of gripping the landing band,
   wherein each of the first and second elastic belts extends laterally outwards from respective ones of the lengthwise edges of said containment assembly in said rear waist region,
   wherein each one of said first and second elastic belts has one end connected to said rear waist region and another end laterally separated outwards from said one end, said gripping devices being provided, respectively, on said another end of each of said elastic belts, and
   wherein said elastic belts comprise a top nonwoven layer portion, a back nonwoven layer portion, and a layer of a portion of elastomer threads placed between said top and back nonwoven layer portions, jointly forming said elastic belts, which have an elasticity of between about 250% to about 500%, and in which said top and back nonwoven layer portions have respirability.

2. The absorbent article according to claim 1, further comprising extension ears disposed in the rear waist region of said containment assembly, wherein each of the first and second elastic belts extends laterally outwards from respective ones of said extension ears.

3. The absorbent article according to claim 1, wherein said elastomer threads are disposed in a zig zag or linear pattern.

4. The absorbent article according to claim 1, wherein said elastic belts have a maximum deformation not greater than about 3.3%.

5. The absorbent article according to claim 1, wherein said elastic belts have an elasticity of up to 280%, with deformation not greater than about 3.3%.

6. The absorbent article according to claim 1, wherein said elastic belts have an elongation of about 280% at a tension of about 32.7 N.

7. The absorbent article according to claim 1, wherein a material of said elastomer threads is selected from the group consisting of LYCRA®, natural or synthetic rubber, latex, SPANDEX® or any other elastomeric element.

8. The absorbent article according to claim 1, wherein the absorbent article is a diaper.

9. The absorbent article according to claim 1, wherein the absorbent article is a training pant, brief or bikini type.

10. The absorbent article according to claim 2, wherein said extension ears are made of a material selected from the group consisting of polypropylene, polyurethane, and any woven sheet or other liquid & gas pervious or impervious sheet materials.

* * * * *